United States Patent
Kriesel et al.

(10) Patent No.: US 7,694,938 B2
(45) Date of Patent: Apr. 13, 2010

(54) DISTAL RATE CONTROL DEVICE

(75) Inventors: Marshall S. Kriesel, Saint Paul, MN (US); Joshua W. Kriesel, San Francisco, CA (US); Alan D. Langerud, Saint Paul, MN (US); Donald B Bivin, Oakland, CA (US)

(73) Assignee: BioQuiddity, Inc., San Francisco, CA (US)

( * ) Notice: Subject to any disclaimer, the term of this patent is extended or adjusted under 35 U.S.C. 154(b) by 1042 days.

(21) Appl. No.: 11/353,598

(22) Filed: Feb. 13, 2006

(65) Prior Publication Data
US 2006/0196552 A1    Sep. 7, 2006

Related U.S. Application Data

(60) Provisional application No. 60/654,440, filed on Feb. 17, 2005.

(51) Int. Cl.
*F16K 5/10* (2006.01)
(52) U.S. Cl. .................. 251/208; 137/385; 137/556
(58) Field of Classification Search .......... 137/487.5, 137/342, 385; 251/205, 206, 208; 604/246, 604/248
See application file for complete search history.

(56) References Cited

U.S. PATENT DOCUMENTS

| | | | |
|---|---|---|---|
| 3,731,681 A | 5/1973 | Blackshear et al. |
| 4,381,006 A | 4/1983 | Genese |
| 4,525,165 A | 6/1985 | Fischell |
| 4,557,728 A | 12/1985 | Sealfon et al. |
| 4,608,042 A | 8/1986 | Vanderveen et al. |
| 4,681,566 A | 7/1987 | Fenton, Jr. et al. |
| 4,755,172 A | 7/1988 | Baldwin |
| 4,772,263 A | 9/1988 | Dorman et al. |
| 4,850,807 A | 7/1989 | Frantz |
| 4,863,429 A | 9/1989 | Baldwin |
| 5,014,750 A | 5/1991 | Winchell et al. |
| 5,098,377 A | 3/1992 | Borsanyi et al. |
| 5,100,389 A | 3/1992 | Vaillancourt |
| 5,176,641 A | 1/1993 | Idriss |
| 5,205,820 A | 4/1993 | Kriesel |
| 5,236,418 A | 8/1993 | Kriesel |
| 5,290,259 A | 3/1994 | Fischer |
| 5,306,257 A | 4/1994 | Zdeb |
| 5,314,405 A | 5/1994 | Kriesel et al. |
| 5,336,188 A | 8/1994 | Kriesel |
| 5,346,476 A | 9/1994 | Elson |
| 5,380,287 A | 1/1995 | Kikuchi et al. |
| 5,411,480 A | 5/1995 | Kriesel |
| 5,419,771 A | 5/1995 | Kriesel |
| 5,484,410 A | 1/1996 | Kriesel et al. |
| 5,499,968 A | 3/1996 | Milijasevic et al. |

(Continued)

*Primary Examiner*—John Rivell
*Assistant Examiner*—Christopher Pilling

(57) ABSTRACT

A distal rate control device, which can be conveniently interposed between a fluid supply line and fluid delivery line for precisely controlling the rate of fluid flow toward the delivery line. The device includes a readily adjustable flow rate control device having a novel flow control plate that can be placed in fluid communication with the fluid supply line and with the fluid delivery line. The flow control plate is provided with a plurality of elongated fluidic flow control channels that are in communication with a rate selector member that is rotatably carried by the device housing. Rotation of the rate selector member places a selected one of the flow control channels in communication with the fluid delivery line.

27 Claims, 26 Drawing Sheets

U.S. PATENT DOCUMENTS

| | | | |
|---|---|---|---|
| 5,514,090 A | 5/1996 | Kriesel et al. | |
| 5,545,139 A | 8/1996 | Kriesel | |
| 5,584,323 A * | 12/1996 | Yamamuro | 137/625.65 |
| 5,620,420 A | 4/1997 | Kriesel | |
| 5,693,018 A | 12/1997 | Kriesel et al. | |
| 5,693,019 A | 12/1997 | Kriesel | |
| 5,720,729 A | 2/1998 | Kriesel | |
| 5,721,382 A | 2/1998 | Kriesel et al. | |
| 5,735,818 A | 4/1998 | Kriesel et al. | |
| 5,741,242 A | 4/1998 | Kriesel | |
| 5,743,879 A | 4/1998 | Kriesel | |
| 5,766,149 A | 6/1998 | Kriesel et al. | |
| 5,779,676 A | 7/1998 | Kriesel et al. | |
| 5,807,323 A | 9/1998 | Kriesel et al. | |
| 5,836,484 A | 11/1998 | Gerber | |
| 5,858,005 A | 1/1999 | Kriesel | |
| 5,885,250 A | 3/1999 | Kriesel et al. | |
| 5,897,530 A | 4/1999 | Jackson | |
| 5,921,962 A | 7/1999 | Kriesel et al. | |
| 5,925,017 A | 7/1999 | Kriesel et al. | |
| 5,957,891 A | 9/1999 | Kriesel et al. | |
| 5,993,425 A | 11/1999 | Kriesel | |
| 6,010,482 A | 1/2000 | Kriesel et al. | |
| 6,027,472 A | 2/2000 | Kriesel et al. | |
| 6,030,363 A | 2/2000 | Kriesel | |
| 6,045,533 A | 4/2000 | Kriesel et al. | |
| 6,063,059 A | 5/2000 | Kriesel | |
| 6,068,613 A | 5/2000 | Kriesel et al. | |
| 6,068,614 A | 5/2000 | Kimber et al. | |
| 6,086,561 A | 7/2000 | Kriesel et al. | |
| 6,090,071 A | 7/2000 | Kriesel | |
| 6,095,491 A * | 8/2000 | Kriesel | 251/206 |
| 6,126,637 A | 10/2000 | Kriesel et al. | |
| 6,126,642 A | 10/2000 | Kriesel et al. | |
| 6,152,898 A | 11/2000 | Olsen | |
| 6,159,180 A | 12/2000 | Kriesel et al. | |
| 6,176,845 B1 | 1/2001 | Kriesel et al. | |
| 6,183,441 B1 | 2/2001 | Kriesel et al. | |
| 6,190,359 B1 | 2/2001 | Heruth | |
| 6,210,368 B1 | 4/2001 | Rogers | |
| 6,236,624 B1 | 5/2001 | Kriesel et al. | |
| 6,245,041 B1 | 6/2001 | Kriesel | |
| 6,257,279 B1 * | 7/2001 | Peltz | 137/637.3 |
| 6,258,062 B1 | 7/2001 | Thielen et al. | |
| 6,270,481 B1 | 8/2001 | Mason et al. | |
| 6,273,133 B1 | 8/2001 | Williamson et al. | |
| 6,277,095 B1 | 8/2001 | Kriesel et al. | |
| 6,293,159 B1 | 9/2001 | Kriesel et al. | |
| 6,319,235 B1 | 11/2001 | Yoshino | |
| 6,355,019 B1 | 3/2002 | Kriesel et al. | |
| 6,391,006 B1 | 5/2002 | Kriesel et al. | |
| 6,394,980 B2 | 5/2002 | Kriesel et al. | |
| 6,398,760 B1 | 6/2002 | Danby | |
| 6,412,484 B1 * | 7/2002 | Izuchukwu et al. | 128/205.22 |
| 6,485,461 B1 | 11/2002 | Mason et al. | |
| 6,537,249 B2 | 3/2003 | Kriesel et al. | |
| 6,542,350 B1 | 4/2003 | Rogers | |
| 6,569,125 B2 | 5/2003 | Jepson et al. | |
| 6,645,175 B2 | 11/2003 | Kriesel et al. | |
| 6,669,668 B1 | 12/2003 | Kleeman et al. | |
| 7,029,455 B2 | 4/2006 | Flaherty | |
| 2005/0038387 A1* | 2/2005 | Kriesel et al. | 604/133 |
| 2005/0277884 A1* | 12/2005 | Kriesel et al. | 604/132 |

* cited by examiner

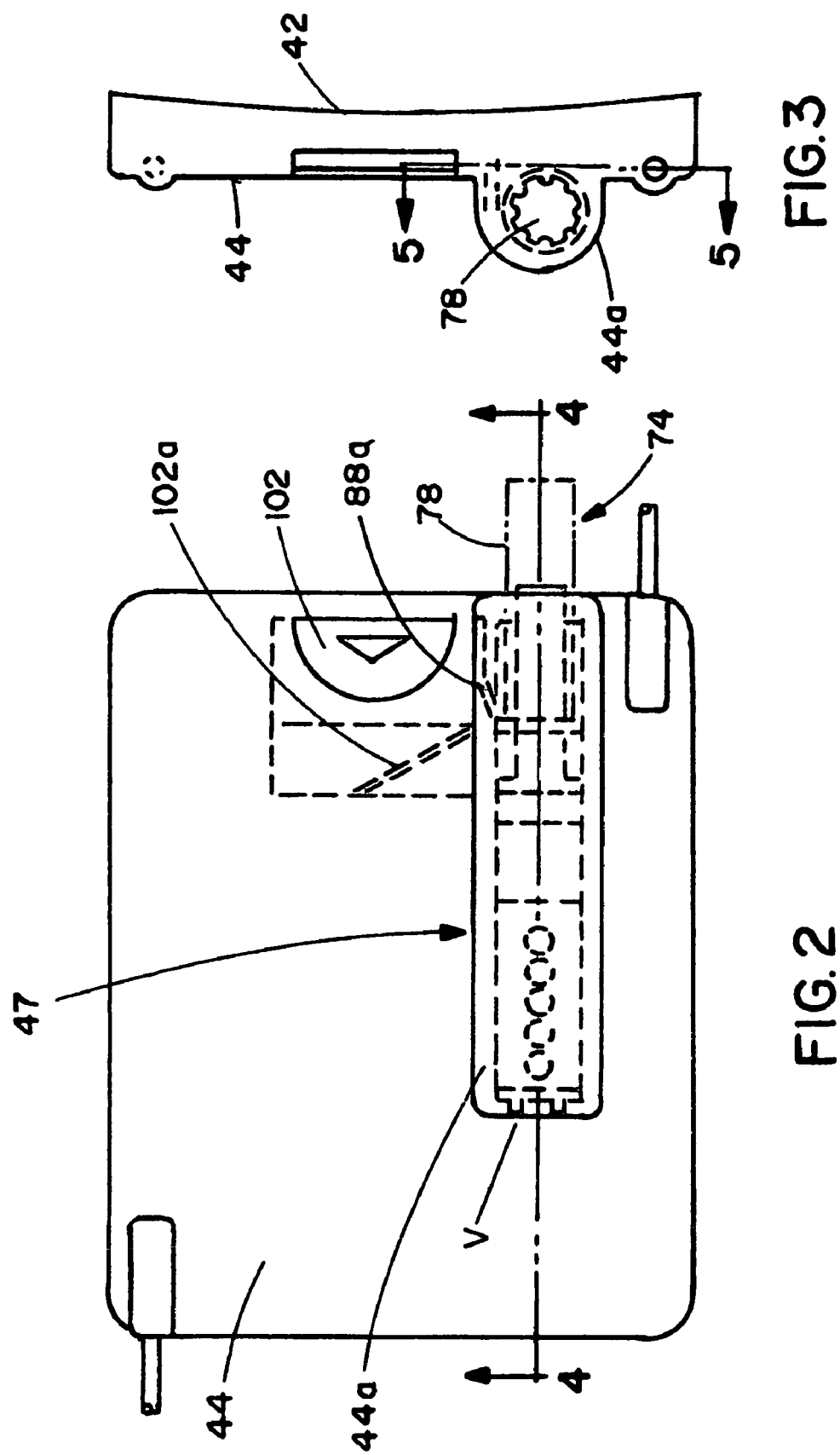

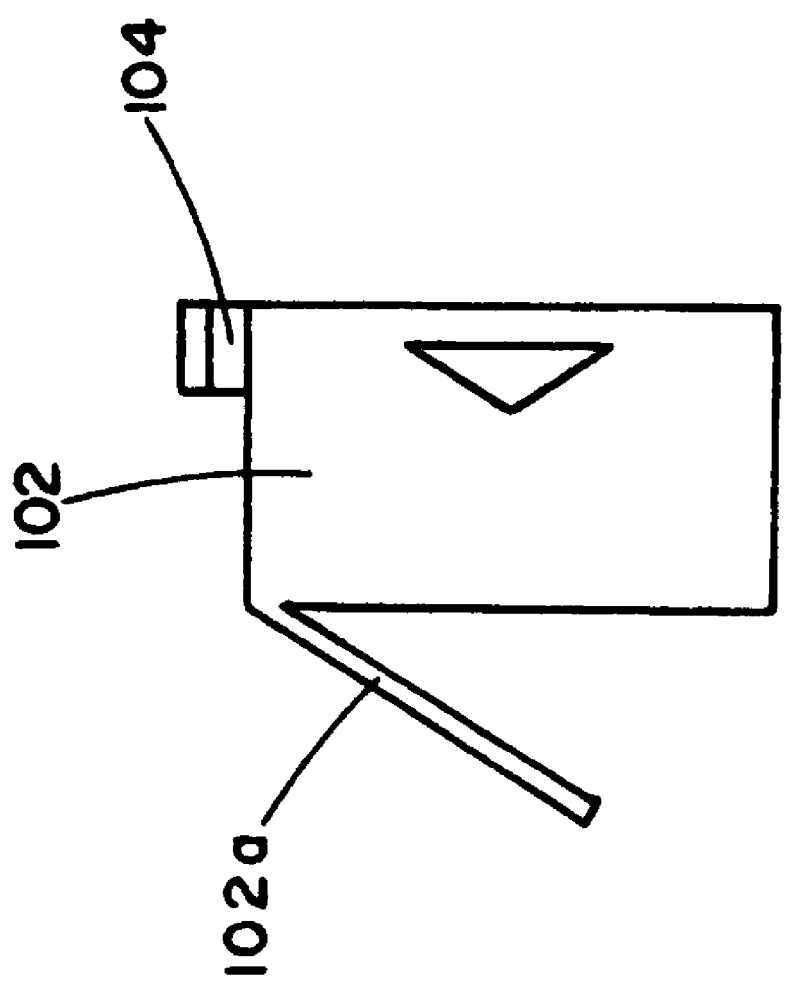

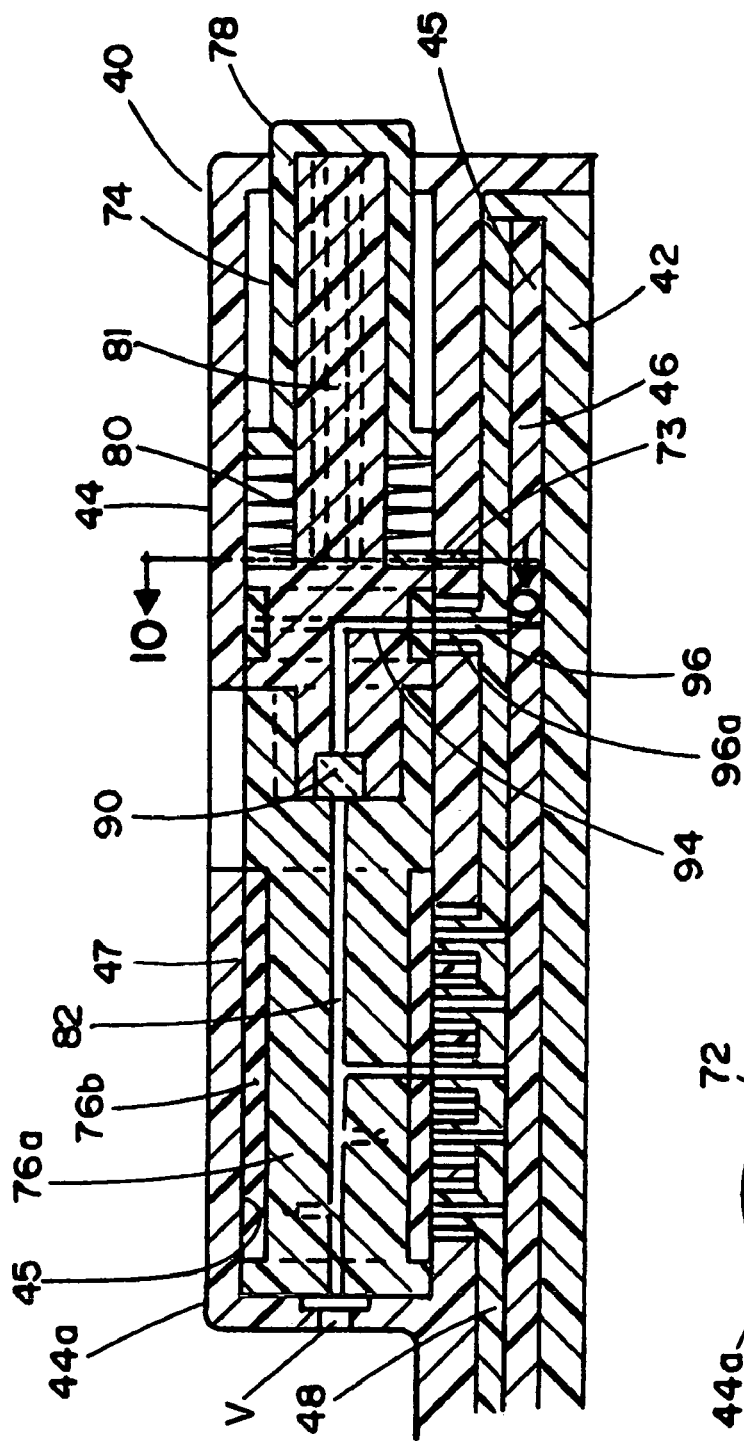
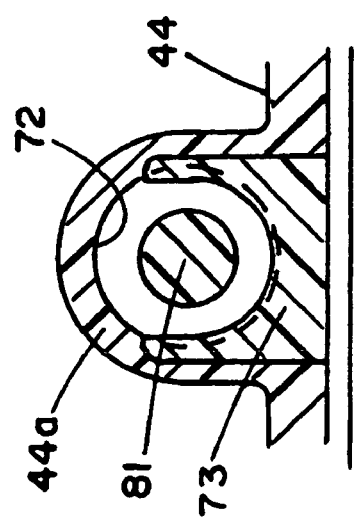
FIG. 9
FIG. 10

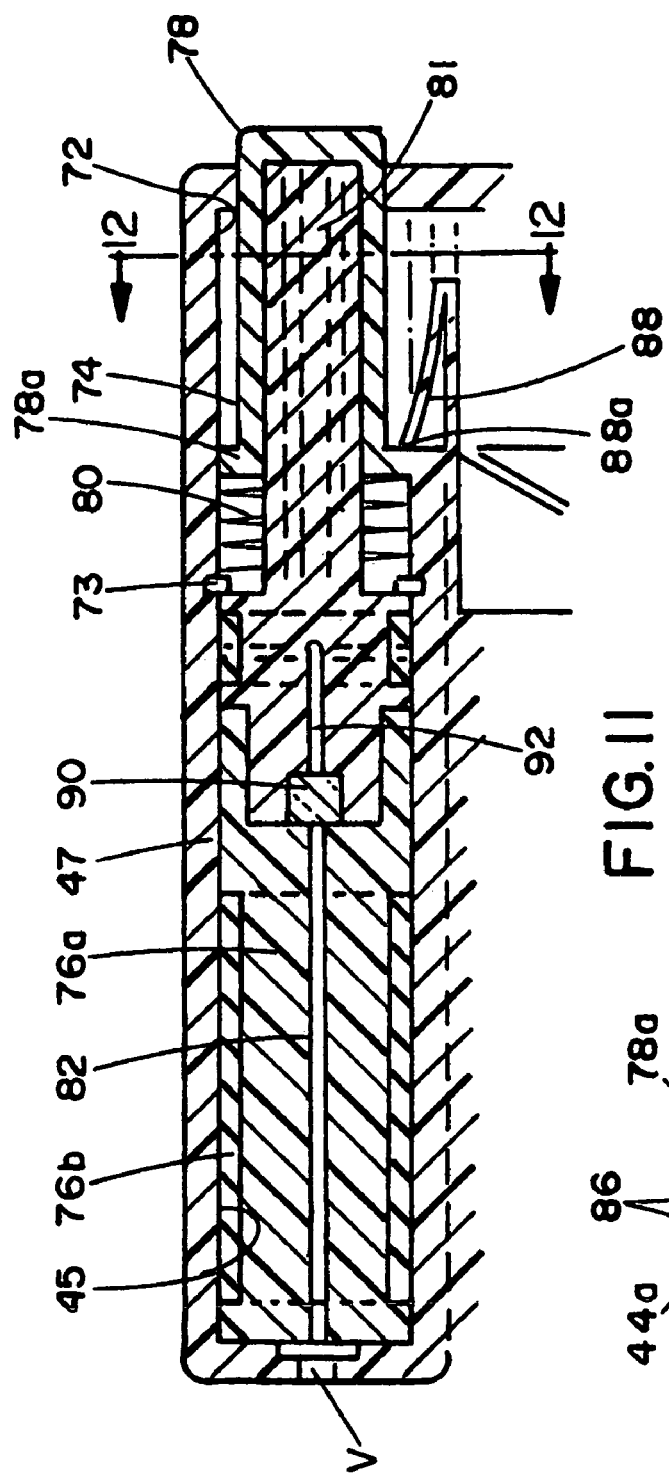
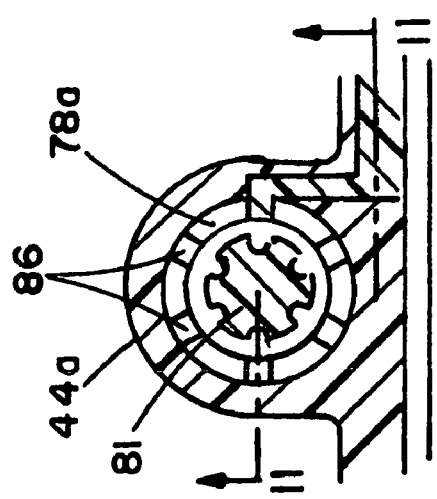
FIG. 11
FIG. 12

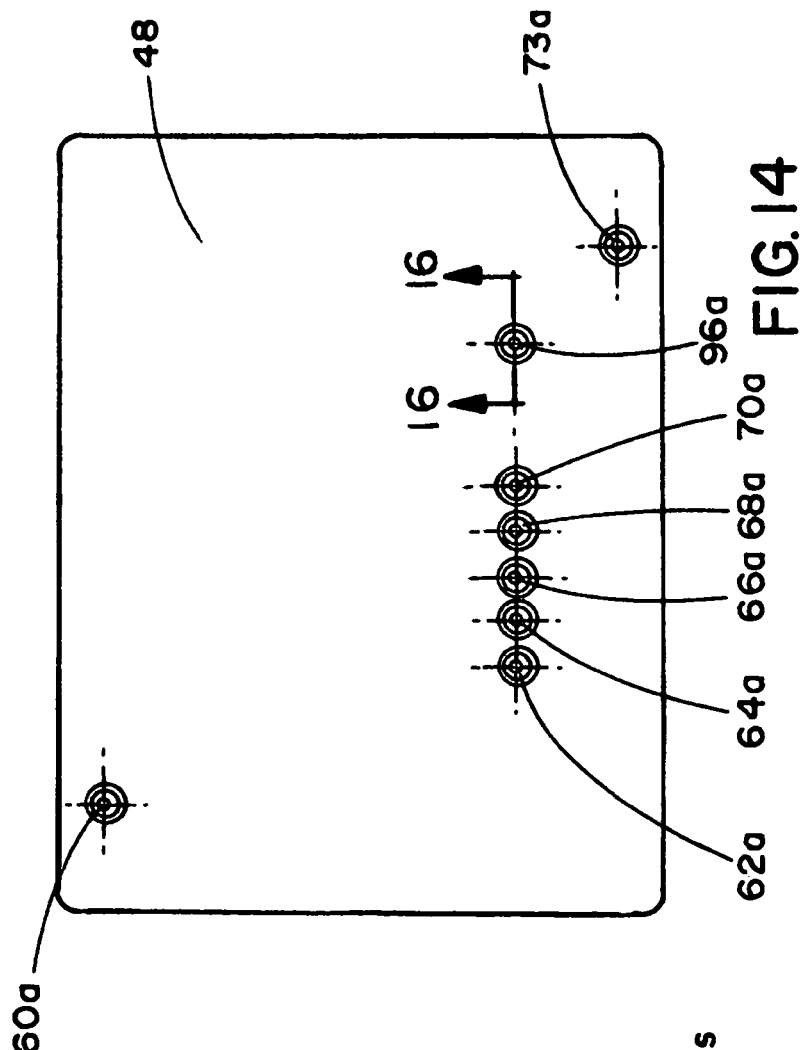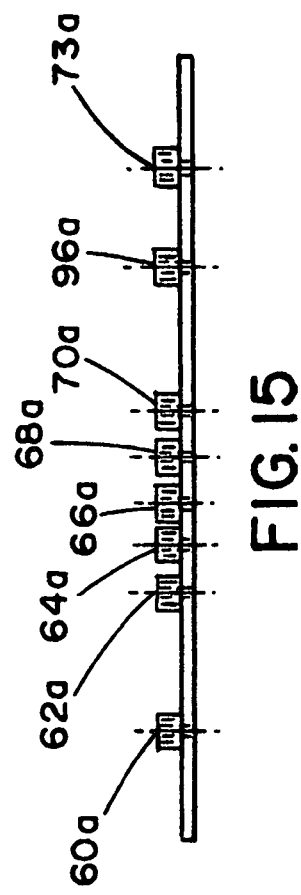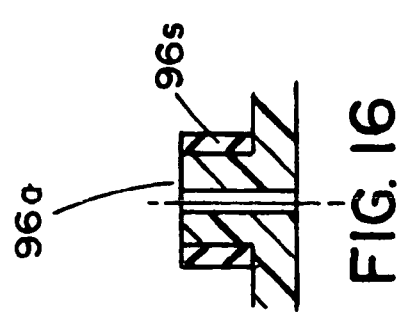

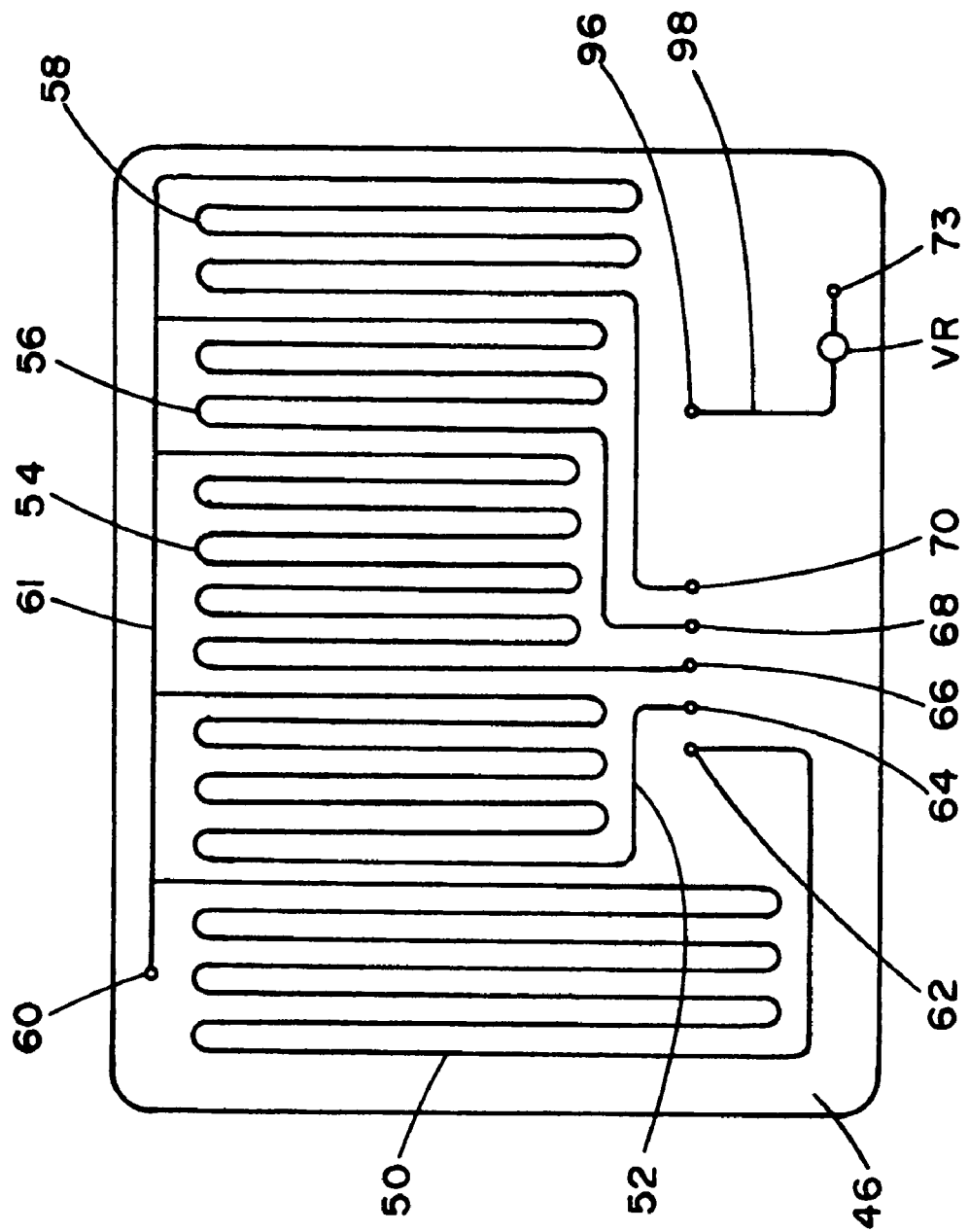

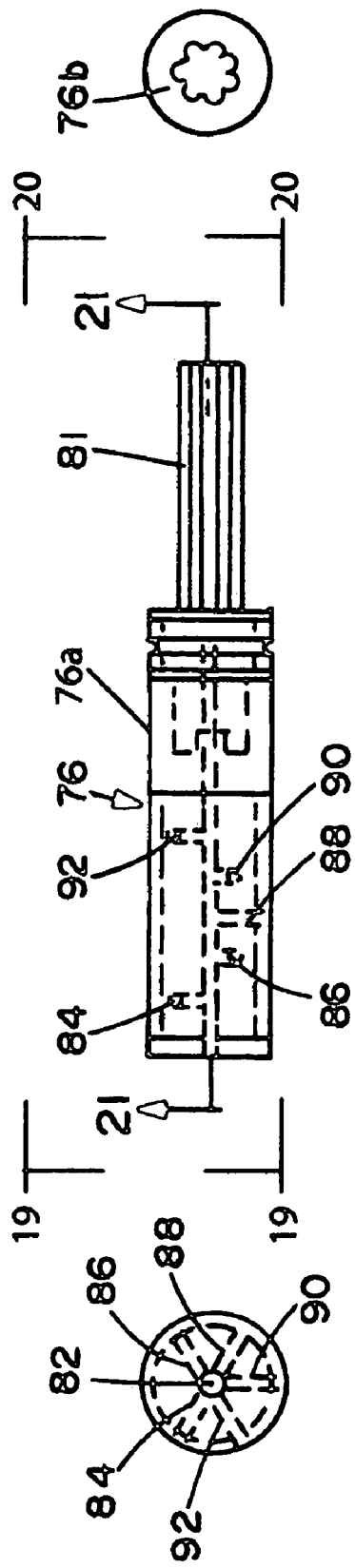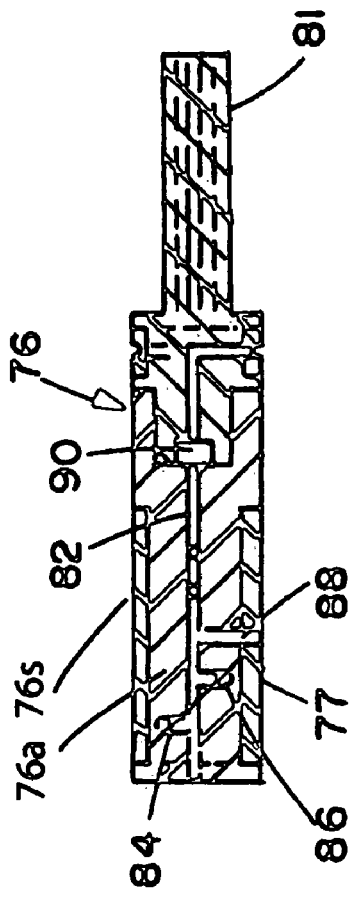

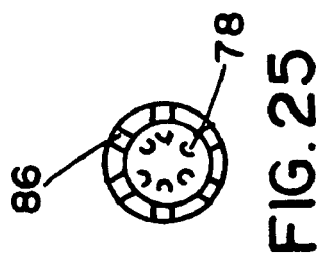
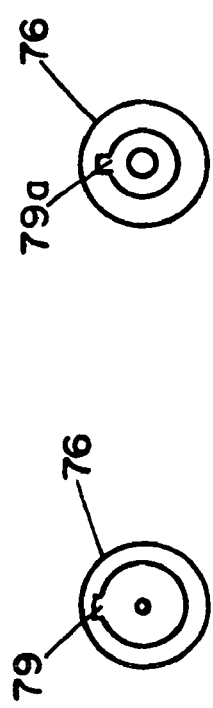
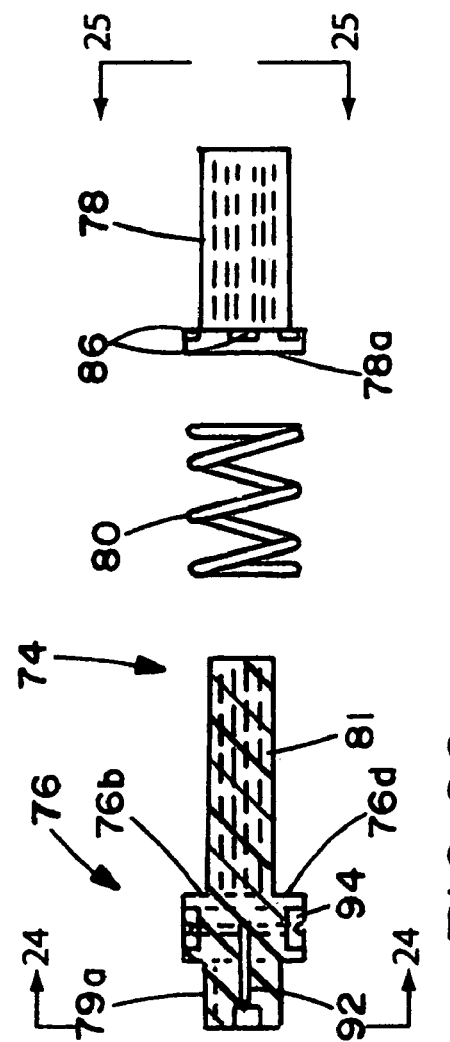
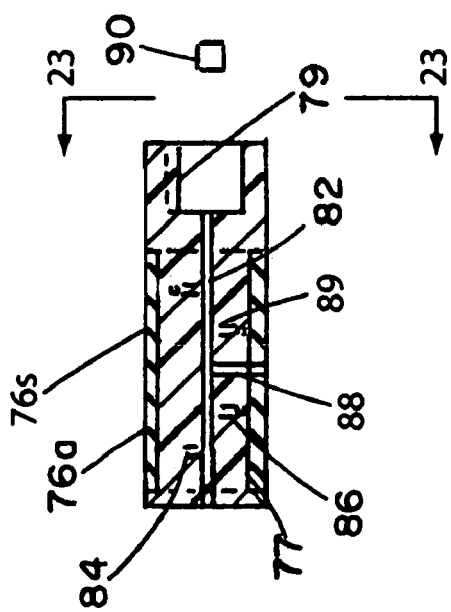

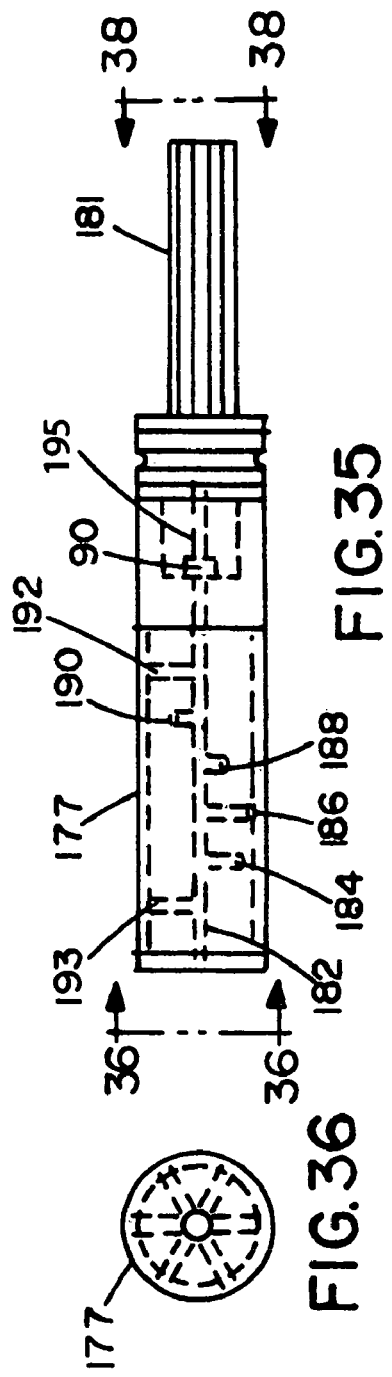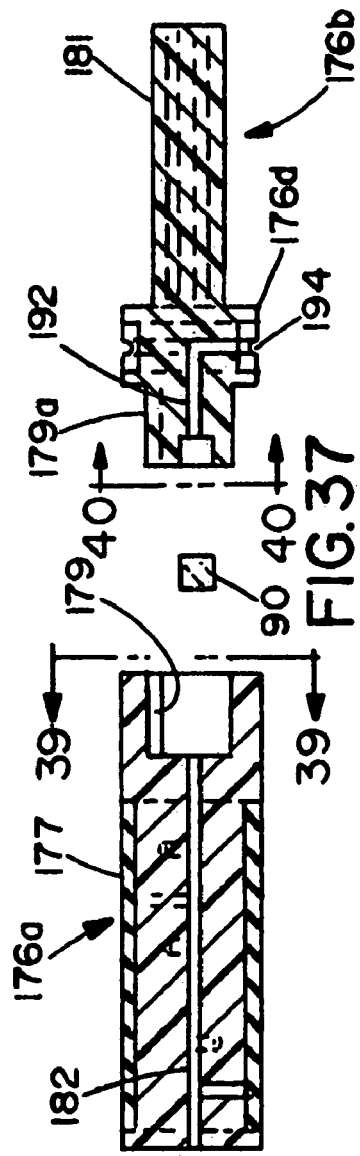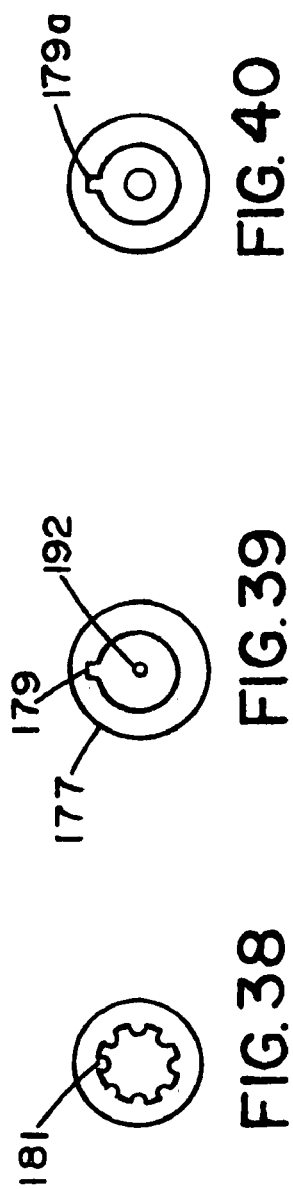

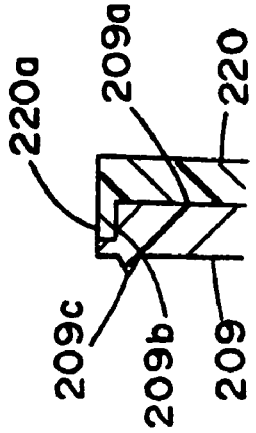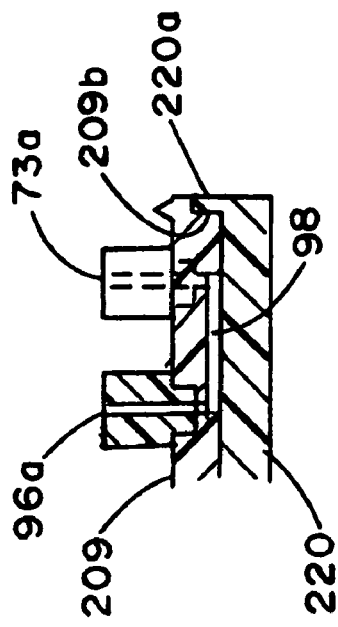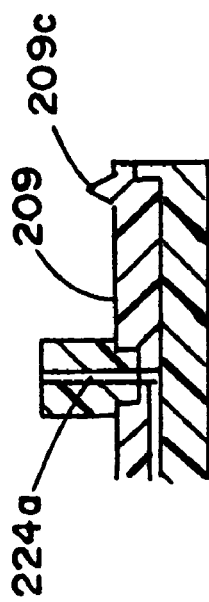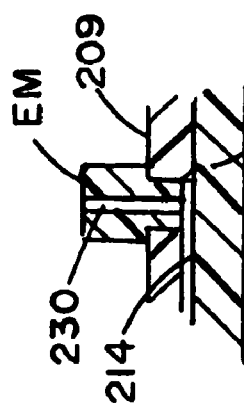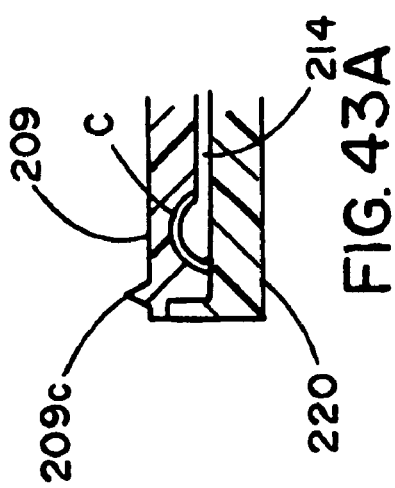

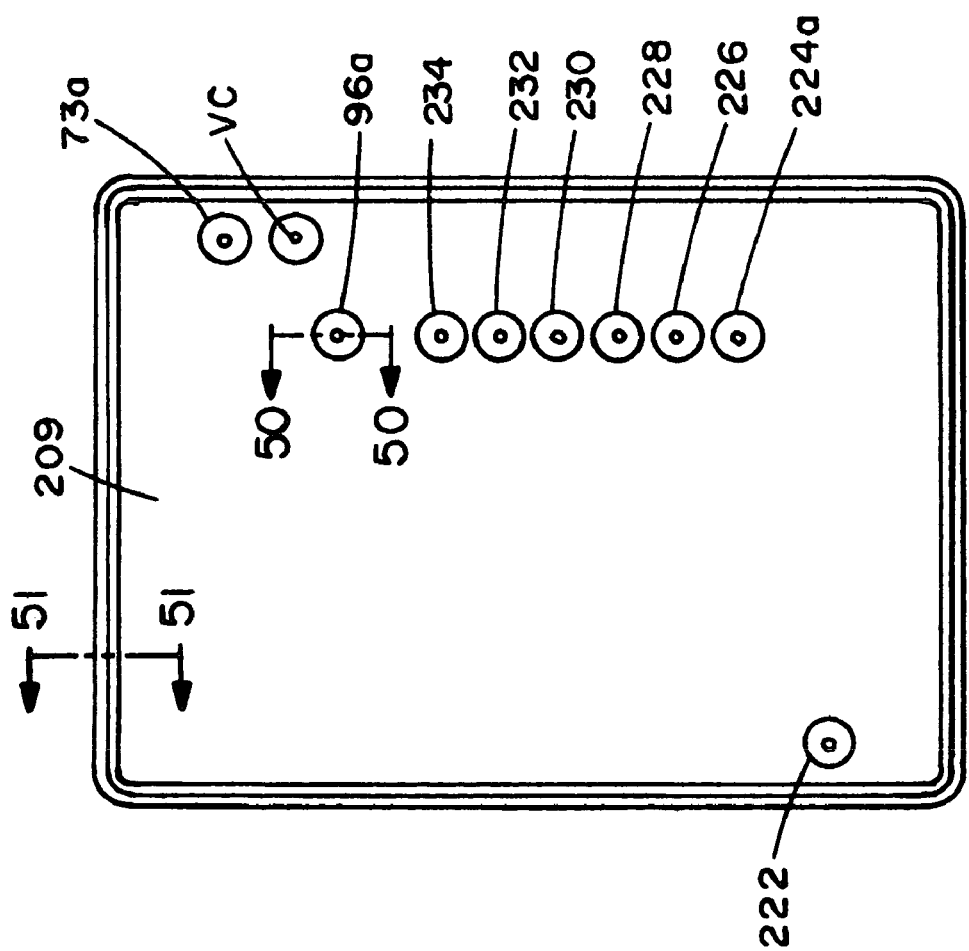

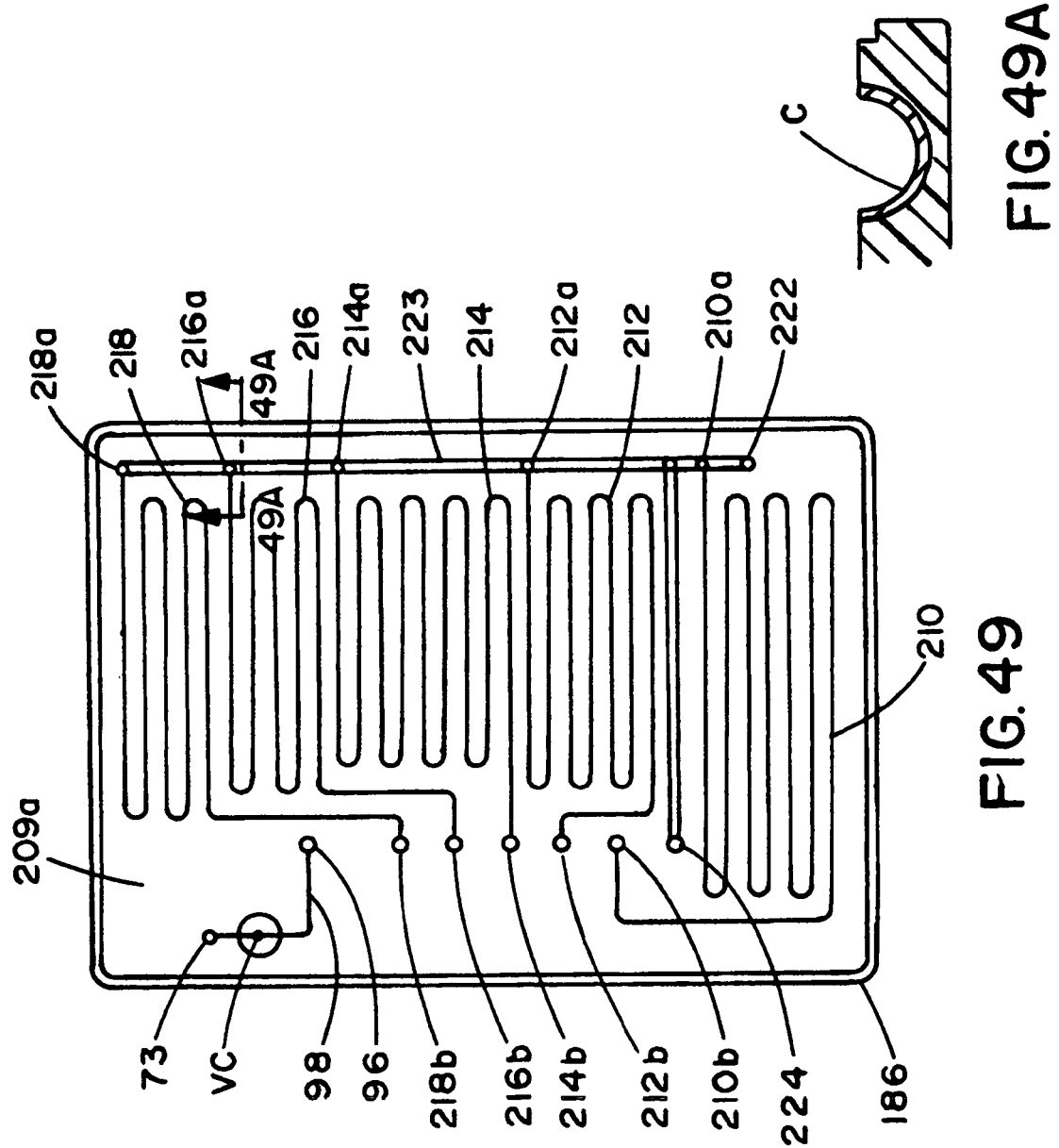

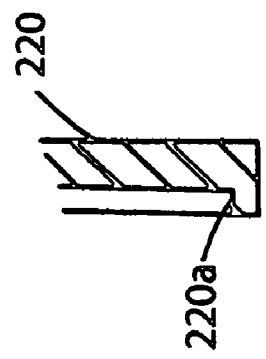
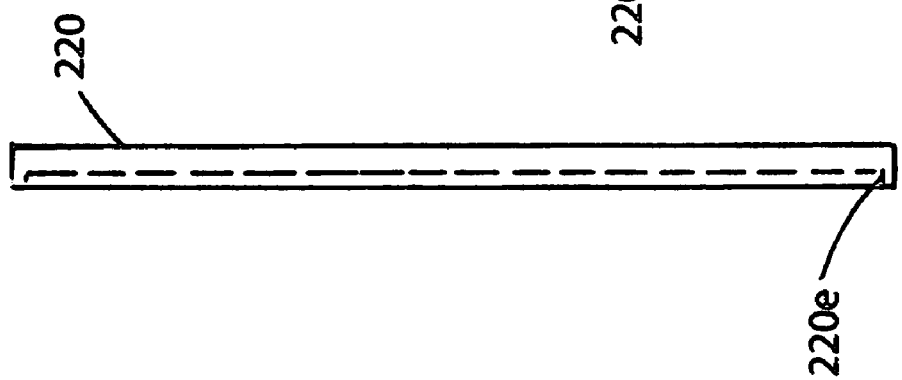
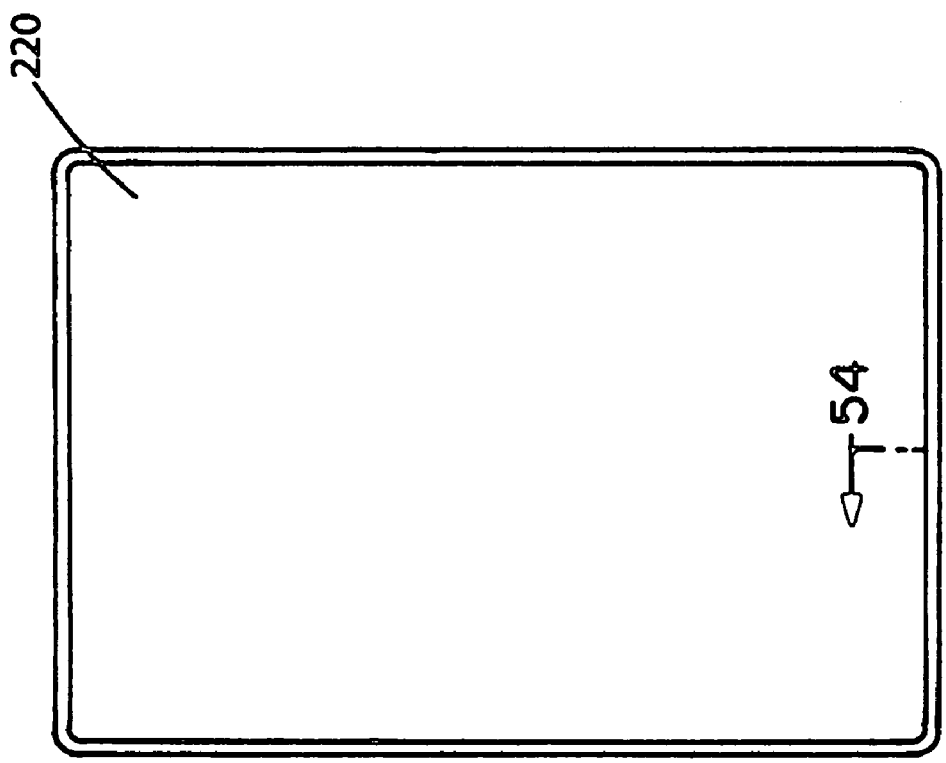

| Channel Type | Flow Rate at 0.5 ATM | Total Channel Length | Cross-sectional Dimensions Width X Depth | Channel Volume | Priming Time at a Pressure of Approximately 0.5 ATM |
|---|---|---|---|---|---|
| Priming channels on the chip | | 8 cm | 1000 μm x 100 μm | .080 ml | |
| Channel in the flow rate selector | | 3 cm | 1000 μm diameter* | .024 ml | |
| Administration line | | 100 cm | 1000 μm diameter* | .785 ml | |
| Priming channel + selector channel + administration line | 0.20 ml/sec | | 40 μm x 100 μm | .89 ml | 4.4 sec |
| 0.1 ml/hr channel | 0.1 ml/hr | 73 cm | 40 μm x 100 μm | $2.9 \times 10^{-3}$ ml | 104.0 sec[1] |
| 0.2 ml/hr channel | 0.2 ml/hr | 36.5 cm | 40 μm x 100 μm | $1.45 \times 10^{-3}$ ml | 25.1 sec |
| 0.3 ml/hr channel | 0.3 ml/hr | 24.3 cm | 40 μm x 100 μm | $9.67 \times 10^{-4}$ ml | 11.6 sec |
| 0.4 ml/hr channel | 0.4 ml/hr | 18.3 cm | 40 μm x 100 μm | $7.32 \times 10^{-4}$ ml | 6.5 sec |
| 0.5 ml/hr channel | 0.5 ml/hr | 14.6 cm | 40 μm x 100 μm | $5.84 \times 10^{-4}$ ml | 4.2 sec[2] |
| 0.6 ml/hr channel | 0.6 ml/hr | 12.2 cm | 40 μm x 100 μm | $4.88 \times 10^{-4}$ ml | 2.9 sec |
| 0.7 ml/hr channel | 0.7 ml/hr | 10.4 cm | 40 μm x 100 μm | $4.16 \times 10^{-4}$ ml | 2.1 sec |
| 0.8 ml/hr channel | 0.8 ml/hr | 9.1 cm | 40 μm x 100 μm | $3.64 \times 10^{-4}$ ml | 1.6 sec |
| 0.9 ml/hr channel | 0.9 ml/hr | 8.1 cm | 40 μm x 100 μm | $3.24 \times 10^{-3}$ ml | 1.3 sec |
| 1.0 ml/hr channel | 1.0 ml/hr | 62.5 cm | 100 μm x 100 μm | $6.25 \times 10^{-3}$ ml | 22.5 sec |
| 2.0 ml/hr channel | 2.0 ml/hr | 31.3 cm | 100 μm x 100 μm | $3.13 \times 10^{-3}$ ml | 5.6 sec |
| 3.0 ml/hr channel | 3.0 ml/hr | 20.8 cm | 100 μm x 100 μm | $2.08 \times 10^{-3}$ ml | 2.5 sec |
| 4.0 ml/hr channel | 4.0 ml/hr | 15.6 cm | 100 μm x 100 μm | $1.56 \times 10^{-3}$ ml | 1.4 sec |
| 5.0 ml/hr channel | 5.0 ml/hr | 12.2 cm | 100 μm x 100 μm | $1.25 \times 10^{-3}$ ml | .9 sec |
| 6.0 ml/hr channel | 6.0 ml/hr | 33.8 cm | 200 μm x 100 μm | $6.76 \times 10^{-3}$ ml | 2.4 sec |
| 10.0 ml/hr channel | 10.0 ml/hr | 35.2 cm | 300 μm x 100 μm | $1.06 \times 10^{-3}$ ml | 3.8 sec |
| 20.0 ml/hr channel | 20.0 ml/hr | 17.6 cm | 300 μm x 100 μm | $5.03 \times 10^{-3}$ ml | 1.0 sec |
| 30.0 ml/hr channel | 30.0 ml/hr | 11.7 cm | 300 μm x 100 μm | $3.53 \times 10^{-3}$ ml | .4 sec |
| 50.0 ml/hr channel | 50.0 ml/hr | 9.9 cm | 400 μm x 100 μm | $3.96 \times 10^{-3}$ ml | 2.9 sec |

FIG. 55

DISTAL RATE CONTROL DEVICE

This is a Non-Provisional Application claiming the benefit of co-pending Provisional Application No. 60/654,440 filed Feb. 17, 2005.

BACKGROUND OF THE INVENTION

1. Field of the Invention

The present invention relates generally to fluid flow rate control devices for controlling the rate of fluid flow from a fluid source to a remote location. More particularly, the invention concerns a novel, readily adjustable flow rate control device having a novel flow control plate that is positioned intermediate a fluid supply line and a fluid delivery line. The flow control plate is provided with a plurality of elongated fluidic flow control channels that are in communication with a rate selector member that is rotatably carried by the device housing. Rotation of the rate selector member places a selected one of the flow control channels in communication with the fluid delivery line and precisely controls the rate of fluid flow from the fluid source toward the remote location.

2. Discussion of the Prior Art

A number of in-line fluid flow controllers for use in controlling the rate of fluid flow from a fluid supply line into a fluid delivery line have been suggested in the past. These types of devices are used in a wide variety of applications where it is necessary to control the rate at which fluid flows from a fluid source to a remote delivery point via fluid supply and delivery lines.

A frequently used application of prior art fluid flow devices is to control the rate of infusion of a fluid medicament from a source of fluid medicament into the body of a patient. Examples of such prior art devices are described in U.S. Pat. No. 6,095,491 issued to one of the present inventors. This patent describes a readily adjustable flow rate control device having a movable flow control member which includes a plurality of spaced-apart flow restrictors which are adapted to be selectively positioned intermediate to a fluid flow path extending between a fluid supply line and a fluid delivery line. In one form of this prior art device the flow restrictors take the form of a plurality of porous rate control frits which can be selectively moved into index with the fluid flow path.

Another prior art fluid flow control device is described in U.S. Pat. No. 5,499,968 issued to Milijasevic, et al. This patent describes various constructions of in-line fluid flow controllers which are adapted primarily for use with a conventional fluid administration set of the type used for infusion of fluid into the body of a patient. In one embodiment, the Milijasevic, et al., fluid flow controllers comprise a housing, a chamber therein and an inlet to and an outlet from the chamber. The housing is adapted to receive therewithin at least one flow restrictor having an orifice configured to control the rate of fluid flow therethrough and into the body of the patient. In an alternate embodiment, the controller is adapted with a series of fluid passageways, which are linked with a series of orifice plates held in position by a wedge.

Another somewhat similar prior art fluid flow rate control device is disclosed in U.S. Pat. No. 4,781,698 issued to Parren. The Parren device comprises a conventional roller clamp, which is connected to a drop chamber. The drop chamber controls the size of the droplets flowing toward the roller clamp and the roller clamp controls the rate of fluid flow through the delivery line. The Parren apparatus includes a disk having a discharge opening which is selectively alignable with one or more drop tubes and includes a flexible edge or wiper means formed around the discharge opening to provide a seal between the disk and the selected drop tube to prevent fluid from seeping between the disk and the mounting plate.

A common drawback of many of the prior art flow controllers is that the controllers are often complex in construction, are difficult and costly to manufacture, are often somewhat unreliable and lack ease of adjustability to quickly and easily vary the rate of fluid through the device. The thrust of the present invention is to overcome these drawbacks by providing a compact, readily adjustable, highly precise flow rate control device which is easy to install within a fluid system, is easy to use and is particularly well-suited for use in connection with medicament dispensers for precisely dispensing medicaments to a patient in a home care environment.

SUMMARY OF THE INVENTION

It is an object of the present invention to provide a compact, easy-to-use flow rate control device, which can be conveniently interposed between a fluid supply line and a fluid delivery line for precisely controlling the rate of fluid flow from the fluid supply toward the delivery line.

More particularly, it is an object of the invention to provide a flow rate control device of the aforementioned character which can be conveniently inserted into an administration set of the character used for infusing fluids into the human body.

Another object of the invention is to provide a flow rate control device as described in the preceding paragraph which comprises a readily adjustable flow rate control device having a novel flow control plate that can be placed in fluid communication with the outlet port of a medicament dispenser. The flow control plate is provided with a plurality of elongated fluidic flow control channels that are in communication with a rate selector member that is rotatably carried by the device housing. Rotation of the rate selector member places a selected one of the flow control channels in communication with the medicament dispenser and in communication with a patient to precisely control the rate of fluid flow toward the patient.

Another object of the invention is to provide a flow rate control device of the type described in the preceding paragraph in which the elongated fluid flow control channels comprise meandering serpentine-like micro channels of various lengths, depths and configurations.

Another object of the invention is to provide a device of the character described which includes priming means for priming the various fluid passageways of the device and purging the fluid passageways of gases that may be contained therein prior to the delivery of the medicinal fluids to the administration line of the device. More particularly an object of the invention is to provide such a device which includes a flow control plate that is provided with a priming channel, that is in communication with the plurality of elongated fluidic flow control channels formed in a rate control member and is also in communication with the rate selector member that is rotatably carried by the device housing.

Another object of the invention is to provide a flow rate control device of the aforementioned character in which the flow rate selector member can be locked against rotation by means of a novel locking mechanism once a particular fluidic flow control channel is selected.

BRIEF DESCRIPTION OF THE DRAWINGS

FIG. 2 is a top plan view of the device.

FIG. 3 is a left-side view of the device.

FIG. 7 is a top plan view of the rate control knob-locking member of the locking mechanism of the device for locking the rate control knob in a selected position.

FIG. 8 is a top plan view of the rate control knob-lock release member of the locking mechanism of the device.

FIG. 9 is an enlarged, cross-sectional view similar to FIG. 4, but rotated 180 degrees.

FIG. 10 is a cross-sectional view taken along lines 10-10 of FIG. 9.

FIG. 11 is a cross-sectional view taken along lines 11-11 of FIG. 10.

FIG. 12 is a cross-sectional view taken along lines 12-12 of FIG. 11.

FIG. 14 is a top plan view of the cover member of the flow rate control assembly of the apparatus.

FIG. 15 is a view taken along lines 15-15 of FIG. 14.

FIG. 16 is an enlarged cross-sectional view taken along lines 16-16 of FIG. 14.

FIG. 17 is a top plan view of one form of the rate control plate of the flow rate control assembly of the device.

FIG. 18 is a side-elevational view of one form of the rate control shaft assembly of the rate control assembly of the apparatus.

FIG. 19 is a view taken along lines 19-19 of FIG. 18.

FIG. 20 is a view taken along lines 20-20 of FIG. 18.

FIG. 21 is a cross-sectional view taken along lines 21-21 of FIG. 20.

FIG. 22 is an exploded, cross-sectional view of the rate control shaft assembly of the invention shown in FIG. 21 along with an exploded view of the cooperating rate control knob assembly of the device of the invention.

FIG. 23 is a view taken along lines 23-23 of FIG. 22.

FIG. 24 is a view taken along lines 24-24 of FIG. 22.

FIG. 25 is a view taken along lines 25-25 of FIG. 22.

FIG. 35 is a side-elevational view of one form of the rate control shaft assembly of the rate control assembly of this latest form of the apparatus of the invention.

FIG. 36 is a view taken along lines 36-36 of FIG. 35.

FIG. 37 is a side-elevational, exploded view of the rate control shaft assembly shown in FIG. 35.

FIG. 38 is an enlarged view taken along lines 38-38 of FIG. 35.

FIG. 39 is an enlarged view taken along lines 39-39 of FIG. 37.

FIG. 40 is an enlarged view taken along lines 40-40 of FIG. 37.

FIG. 43 is an enlarged cross-sectional view taken along lines 43-43 of FIG. 42.

FIG. 43A is a view similar to FIG. 43, but showing the compression of the elastomeric cover ports as the rate control assembly is mated with the device housing.

FIG. 44 is an enlarged cross-sectional view taken along lines 44-44 of FIG. 42.

FIG. 45 is an enlarged cross-sectional view taken along lines 45-45 of FIG. 42.

FIG. 46 is an enlarged cross-sectional view taken along lines 46-46 of FIG. 42.

FIG. 47 is a side view of the cover member of the flow rate control assembly of the apparatus shown in FIG. 42.

FIG. 48 is a top plan view of the cover member of the flow rate control assembly of the apparatus illustrated in FIG. 41.

FIG. 49 is a bottom plan view of the cover member of the flow rate control assembly of the apparatus illustrated in FIG. 41.

FIG. 49A is a greatly enlarged cross-sectional view of one of the fluidic micro channels of the device showing a special coating covering the surface of the micro channel.

FIG. 50 is an enlarged view taken along lines 50-50 of FIG. 48.

FIG. 51 is an enlarged view taken along lines 51-51 of FIG. 48.

FIG. 52 is a top plan view of the base member the flow rate control assembly of this latest form of the invention.

FIG. 53 is a side view of the base member of the flow rate control assembly of this latest form of the invention.

FIG. 54 is an enlarged cross-sectional view taken along lines 54-54 of FIG. 52.

FIG. 55 is a generally tabular view illustrating the fluidic properties of one form of the fluid rate control member, or rate control chip, of the form of the flow rate control device shown in FIG. 27.

DESCRIPTION OF THE INVENTION

Figure 1:
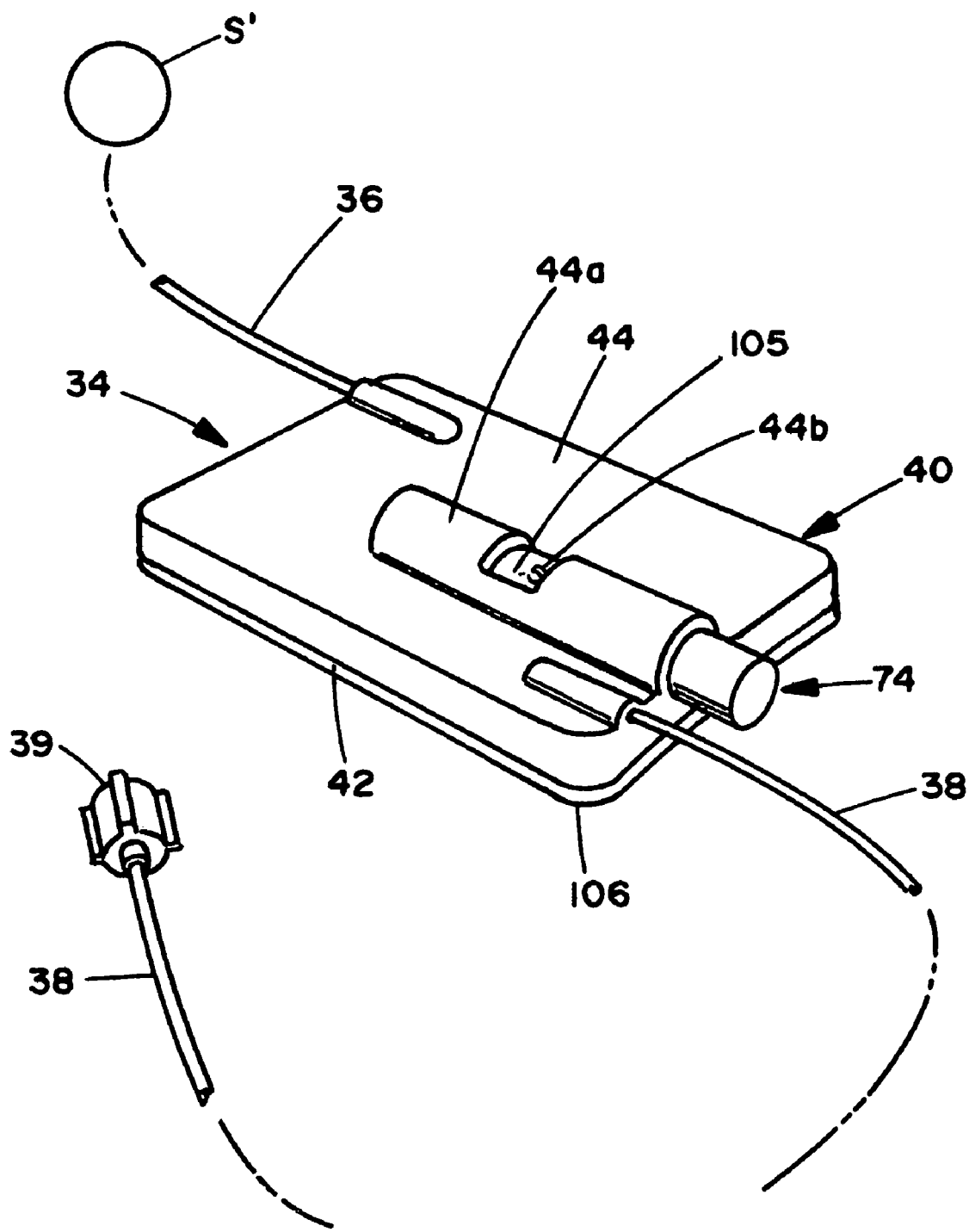
FIG. 1 is a generally perspective view of one form of the in-line flow rate control device of the invention.
Figure 4:
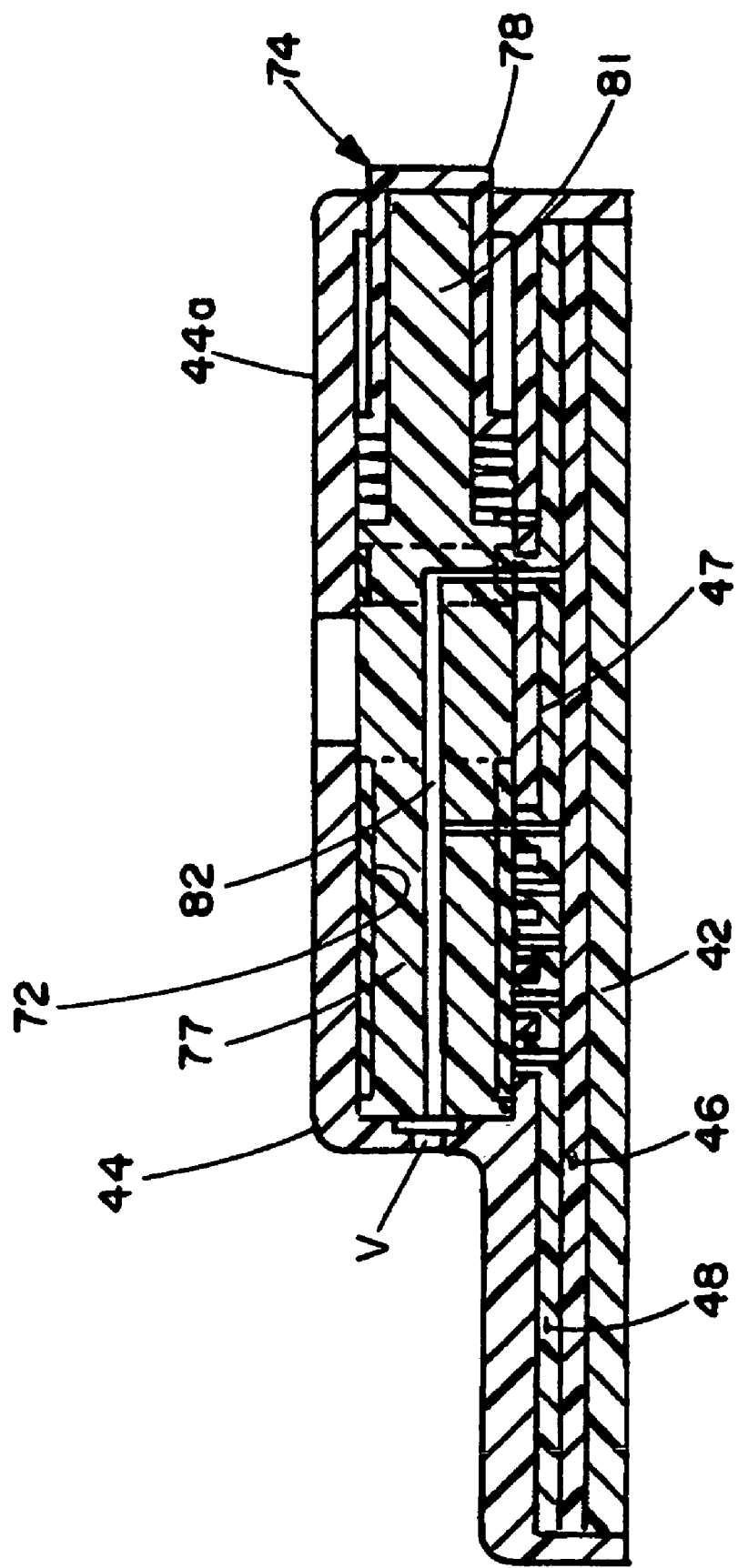
FIG. 4 is a cross-sectional view taken along lines 4-4 of FIG. 2.

Referring to the drawings and particularly to FIGS. 1 through 13, one form of the fluid flow rate control device of the present invention is there illustrated and generally designated by the numeral 34. As illustrated in FIG. 1, the device is adapted to be interposed between a fluid supply line 36 which is interconnected with a source of fluid under pressure "S" and a fluid delivery line 38 which can be interconnected via luer connector 39 with a remote site to which the fluid is to be delivered at a controlled rate.

Figure 13:
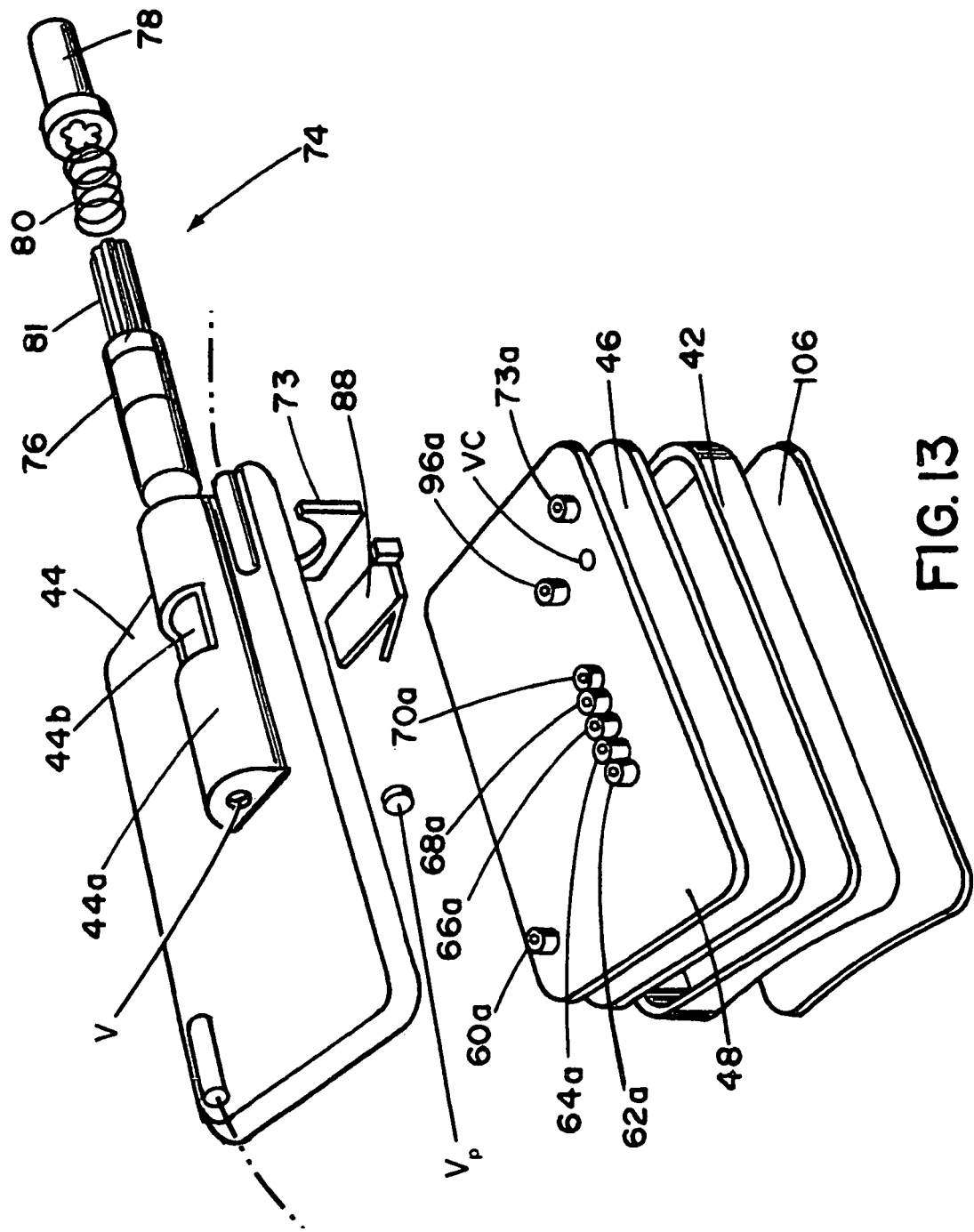
FIG. 13 is a generally perspective, exploded view of the device shown in FIGS. 1 through 4.

As best seen in FIGS. 9 and 13, the device of the present form of the invention comprises a hollow housing 40 which is made up of a base portion 42 and an interconnected cover portion 44. Base portion 42 cooperates with cover 44 to define an internal chamber 45. Disposed within chamber 45 is one portion of the important flow control means of the invention for controlling fluid flow from the fluid supply line 36 toward the fluid delivery line 38. In the embodiment of the invention shown in the drawings, the flow control means comprises a flow rate control assembly, generally designated as 47, which is housed within chamber 45 and a cooperating selector means for selecting the desired rate of fluid flow from the fluid source toward the fluid delivery line.

Considering first the flow rate control assembly 47, this important component of the flow control means comprises a rate control base or plate 46 and an interconnected rate control cover 48 (FIG. 13). As best seen in FIG. 17, rate control base 46 is provided with a plurality of fluidic micro channels identified as 50, 52, 54, 56 and 58. Each of the fluidic micro channels is in communication with an inlet 60 via a passageway 61 and each is provided with an outlet 62, 64, 66, 68, and 70 respectively. These outlets align with upstanding cover outlet ports 62a, 64a, 66a, 68a, and 70a respectively (see FIG. 13) when the flow rate control assembly is assembled together in the manner illustrated in FIG. 14. Each outlet port is provided with sealing means in the form of an elastomeric sleeve "SS" (See FIG. 14) to prevent fluid leakage about the ports. As also shown in FIG. 9, when the flow rate control assembly is assembled together, cover inlet port 60a aligns with rate control plate inlet 60. As will be presently discussed, each of the outlet ports formed in cover 46 can be placed in selective communication with cover outlet port 73a (FIGS. 14 and 15) and with the fluid delivery line 38 by manipulation of the rate control means of the invention.

It is to be understood that the fluidic micro channels formed in rate control base 46 may be of different sizes, lengths and cross-sectional areas as shown in FIG. 17. Further, the flow control fluidic micro channels may be rectangular in cross section, or alternatively, can be semicircular in cross section, U-shaped in cross section, or they may have any other cross-sectional configuration, including varying cross-sectional configurations, that may be appropriate to achieve the fluid flow characteristics that are desired in the particular end-use application. Additionally, the surface characteristics of the channels may be tailored to impart desired flow characteristics.

As best seen in FIGS. 1, 12 and 13, cover 44 is provided with an upraised portion 44a that defines an elongated, generally cylindrically-shaped chamber 72 (FIG. 12). Sealably receivable within chamber 72 and supported by a retainer member 73, is the second component of the flow control means of the invention, namely the selector means, or rate control selector assembly 74. As best seen by referring to FIG. 22, this important rate control selector assembly includes a rate control shaft assembly 76, a cooperating control knob 78 and an operating spring 80. As illustrated in the drawings, rate control shaft assembly 76 includes a selector portion 76a and a control portion 76b. Surrounding portion 76a is sealing means, shown here as an elastomeric sleeve 76s, which functions to seal shaft 76a relative to the housing 44a (FIG. 9). As indicated in FIG. 22, selector portion 76a includes a generally cylindrically-shaped rate control shaft 77 that is provided with a longitudinally-extending fluid flow passageway 82 and a plurality of radially-extending passageways 84, 86, 88, 90 and 92 that communicate with passageway 82 (FIG. 19).

In a manner presently to be described, rotation of the rate control shaft assembly 76 within chamber 72 will permit a selected one of the radially-extending passageways formed in shaft 77 to be aligned with a selected one of the outlet ports of cover 46 and also with a selected one of the fluidic micro channels formed in rate control base 46. To ensure proper mating of the selector portion 76a and the control portion 76b, the selector portion includes a groove 79 and the control portion includes a spline 79a which is received within groove 79 (see FIGS. 23 and 24).

As indicated in FIGS. 18, 20, 22 and 25, the shank portion 81 of the rate control portion 76b of the rate control assembly is knurled and control knob 78 is grooved (FIG. 21) so that when the control knob is mated with the control portion 76b in the manner shown in FIGS. 9 and 10, rotation of the control knob will impart rotation to the selector portion 76a of the rate control shaft assembly. As previously mentioned, controlled rotation of selector portion 76a will cause one of the radially-extending passageways formed within shaft 77 to be moved into fluid communication with a selected one of the outlets of the fluidic rate control channels formed in the rate control plate 46.

Before further discussion of the operation of the selector means of the invention, the details of the construction of the rate control plate 46 and the various methods of making the rate control plate will be considered. With respect to the materials to be used in constructing the rate control plate, medical grade polymers are the materials of choice. These types of polymers include thermoplastics, duroplastics, elastomers, polyurethanes, acrylics and epoxies. In other variations, the materials used for the flow control plate may be made of glass, silica, or silicon. In further variations, the flow control component may be made of metals or inorganic oxides.

Using the foregoing materials, there are several ways that the flow control channels can be made. These include injection molding, injection-compression molding, hot embossing, casting, laser ablation and like techniques well known to those skilled in the art. The techniques used to make these imbedded fluid channels are now commonplace in the field of microfluidics, which gave rise to the lab-on-a-chip, bio-MEMS and micro-total analysis systems (μ-TAS) industries. Additionally, depending on the size of the fluid channels required for a given flow rate, more conventional injection molding techniques can be used.

The first step in making the channels using an injection molding or embossing process is a lithographic step, which allows a precise pattern of channels to be printed on a "master" with lateral structure sizes down to 0.5 μm. Subsequently, electroforming is performed to produce the negative metal form, or mold insert. Alternatively for larger channel systems, precision milling can be used to make the die mold insert directly. Typical materials for the mold insert or embossing tool are nickel, nickel alloys, steel and brass. Once the mold insert is fabricated, the polymer of choice may be injection molded or embossed to yield the desired part with imprinted channels.

Alternatively, channels can be made by one of a variety of casting processes. In general, a liquid plastic resin, for example, a photopolymer can be applied to the surface of a metal master made by the techniques described in the preceding paragraph and then cured via thermal or ultraviolet (UV) means. After hardening, the material is then "released" from the mold to yield the desired part. Additionally, there are similar techniques available that utilize CAD data of the desired channel configuration and direct laser curing of a liquid monomer to yield a polymerized and solidified part with imbedded channels. This process is available by contract, from, by way of example, MicroTEC, GmbH of Duisburg, Germany.

In order to seal the flow control channels, a planar top plate may be used. In this instance, the channel system may be sealed with a top plate, which is here defined as any type of suitable cover that functions to seal the channels. The top plate may be sealably interconnected with the base plate which contains the flow channels by several means, including thermal bonding, sonic welding, laser welding, adhesive bonding with vacuum application and other bonding techniques using plasma deposition.

Thermal bonding may be performed by using a channel base plate material and planar top cover that are made of similar polymeric materials. In this case the two substrates are placed in contact with one another, confined mechanically and heated to 2-5° C. above their glass transition temperature. Following a holding period sufficient enough for the polymer molecules of the two surfaces to interpenetrate with one another, the temperature is slowly reduced and a stress-free bonded interface with imbedded micro channels is yielded.

Additionally, the top plate may be bonded to the base plate through the use of one or more suitable bonding materials or adhesives. The bonding material or adhesive may be of the thermo-melting variety or of the liquid or light curable variety. For thermo-melting adhesives, the adhesive material is melted into the two opposed surfaces, thereby interpenetrating these surfaces and creating a sealed channel structure.

Further, liquid curable bonding materials or adhesives and light curable bonding materials or adhesives may be applied to one of the surfaces, for example the top plate. Subsequently, the other surface is brought into contact with the coated surface and the adhesive is cured by air exposure or via irradiation with a light source. Liquid curable bonding materials or adhesives may be elastomeric, for example, thermoplastic elastomers, and natural or synthetic rubbers, polyurethanes, and silicones. Elastomeric bonding materials may or may not require pressure to seal the channel system. They may also provide closure and sealing to small irregularities in the opposed surfaces by conforming to the substrates of the channel system.

A channel system may also be formed and sealed in cases where two surfaces are being joined and one of the surfaces has one or more apertures. In order to promote bonding between these two surfaces, a vacuum may be applied to the apertures. Bonding may then be accomplished by thermal methods or after previously having applied a bonding material or adhesive.

While the rate control plate can be constructed in various sizes, a rate control chip which is rectangular in shape and approximately 11 cm long and approximately 5 cm wide is suitable for the present application. Similarly, while the depth of the channels can vary depending upon the end-use of the device, as a general rule the depth of the channels is on the order of approximately 1-1000 μm.

As previously mentioned, the cross section of the set of channels may vary in area over the members of the set of individual channels so as to achieve the specified flow rate of a particular channel. The cross section may also vary over the length of any particular channel so as to achieve the specified flow rate for the particular channel. Some examples of typical channel cross sections are square, rectangular, elliptical, circular, semi-circular and semi-elliptical. Channel cross sections may also be more complicated than those noted explicitly here.

A typical fluidic chip will be able to deliver fluid at five specified flow rates as, for example 0.25, 0.5, 1.0, 2.0 and 5.0 ml/hr. and greater for optimum performance, the flow rate should be constant and within 10% of the desired specified value at room temperature.

In operation, the flow of fluid (aquous and non-aquous) through the flow control channels is controlled by taking advantage of the viscous drag imposed on the moving fluid by the walls of the channels. For a given imposed pressure and channel cross section the longer the channel the smaller the flow rate. The pressure required to achieve the desired flow rates in the micro channels is preferably in the range of from 0.01 to 1 ATM. However, for some applications it may be desirable to exceed these limits.

The path that the micro channels take in any given rate control plate may be straight, a single meander or two or more meanders. The turns of the meanders may be of any angle from approximately 45° to approximately 220°. The runs of straight path between turns of the meanders may be of any length that the chip can accommodate, but these straight runs would typically be from 50 μm to 500 μm in length.

Another important feature of the invention comprises locking means for locking the selector means in position after a particular fluid flow micro channel has been selected by means of the controlled rotation of the selector knob 78. As indicated in FIGS. 22 and 25, selector knob 78 includes a foreword, enlarged diameter portion 78a that is provided with a plurality of circumferentially-spaced-apart indexing cavities 86. Cavities 86 are adapted to receive the end 88a of a locking, yieldably deformable leaf spring 88 when knob 78 has been rotated to the selected position and then pushed inwardly of chamber 72 from the first extended position shown in FIG. 6 to the second position shown in FIG. 5. A biasing means, shown here as a coil spring 80 which circumscribes shank portion 81 of control portion 76b (see FIGS. 5 and 6) functions to continuously urge the control knob into the extended starting position. Once the distal end of the locking spring 88 is received within the selected indexing cavity in the manner illustrated in FIG. 11, control knob 78 is locked against rotation and is retained in its inward position within chamber 72.

With the locking means in the locked position shown in FIG. 11, fluid will continue to flow from the source of fluid, through the selected rate control micro channel and into the selected aligned radial passageway formed and selector portion 76a of the selector means. From the selected radial passageway, the fluid will flow into axial passageway 82, through a filter 90 (FIG. 22) which is carried by the control knob shaft assembly 76, into an axially-extending fluid passageway 92 formed in control portion 76b and then into an annular passageway 94 formed in the enlarged diameter portion 76d of control portion 76b.

Figure 26:
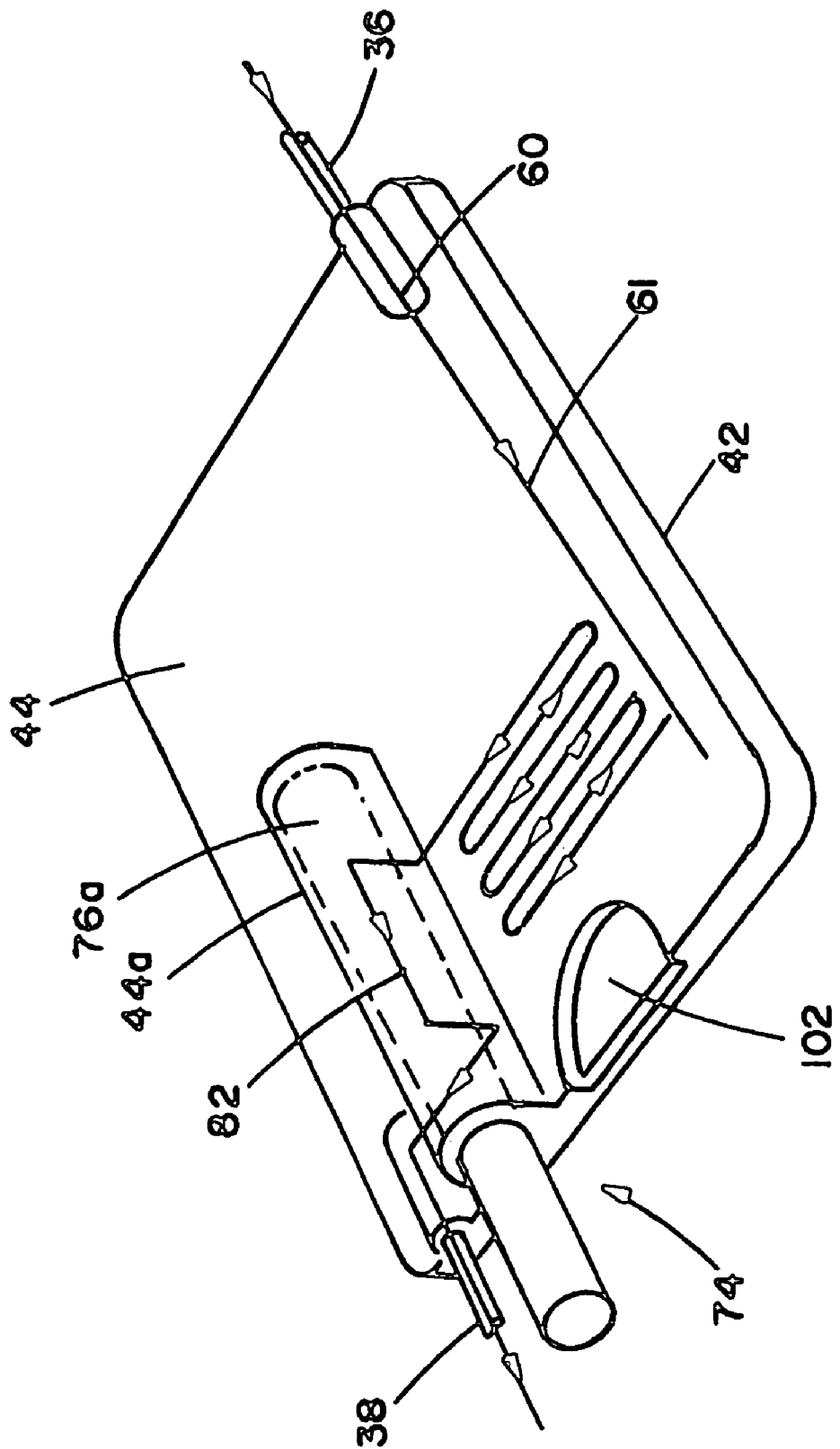
FIG. 26 is a generally perspective, diagrammatic view showing the fluid flow path through the apparatus of the invention shown in FIG. 1.

It is to be observed that, once fluid from the fluid source enters inlet 60 of the rate control plate, each of the fluidic micro channels of the fluid flow path will fill with fluid via passageway 61 so that when the selector means is aligned with one of the outlets of the fluidic micro channels, the fluid can flow freely into the selector portion of the selector means via one of the radially-extending fluid passageways formed in the selector portion 76a (see FIG. 26). The filter 90, which filters the fluid flowing through the fluid flow path toward the fluid delivery line, can be constructed from any suitable sintered metal, glass, ceramic, porous polymer or like material of a character well known to those skilled in the art.

From annular passageway 94, the fluid will flow at a controlled rate through the fluid flow path into an inlet port 96a formed in cover 48 and then into an inlet 96, which is formed in rate control plate 46 and is aligned with inlet port 96a (see FIGS. 9 and 17). Surrounding the outer surface of inlet port 96a is an elastomeric sleeve 96s (FIG. 16), which functions to prevent fluid leakage about the port. Similar sealing sleeves "SS" surround upstanding ports 62a, 64a, 66a, 68a and 70a (FIG. 14). These sleeves comprise a part of the port sealing means of one form of the invention. From inlet 96, the fluid will flow to outlet 73 via a passageway 98 formed in rate control plate 46, into outlet port 73a and then from the fluid flow path into the fluid delivery line 38 which is in communication with outlet port 73 (see FIG. 26).

Figure 5:
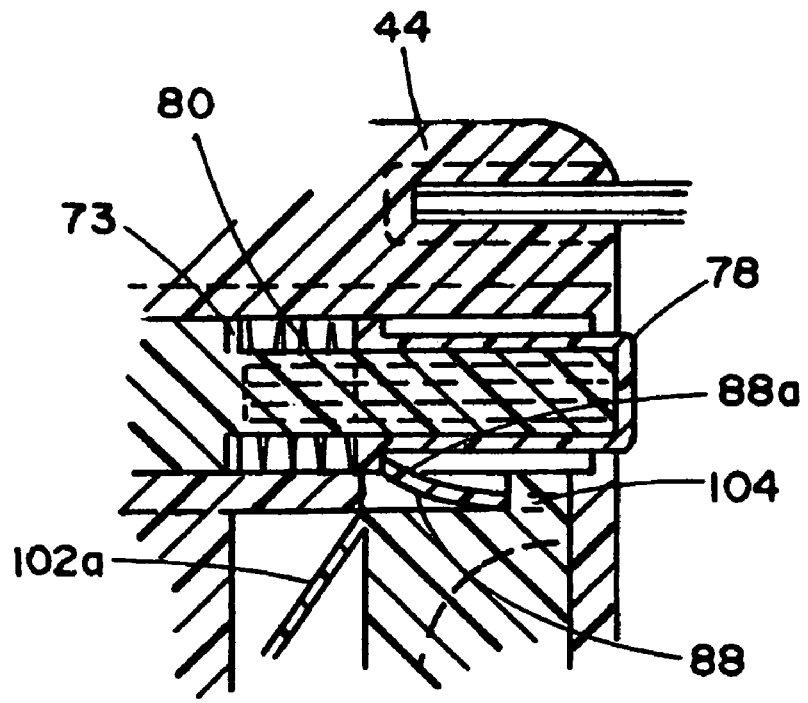
FIG. 5 is a cross-sectional view taken along lines 5-5 of FIG. 3.
Figure 6:
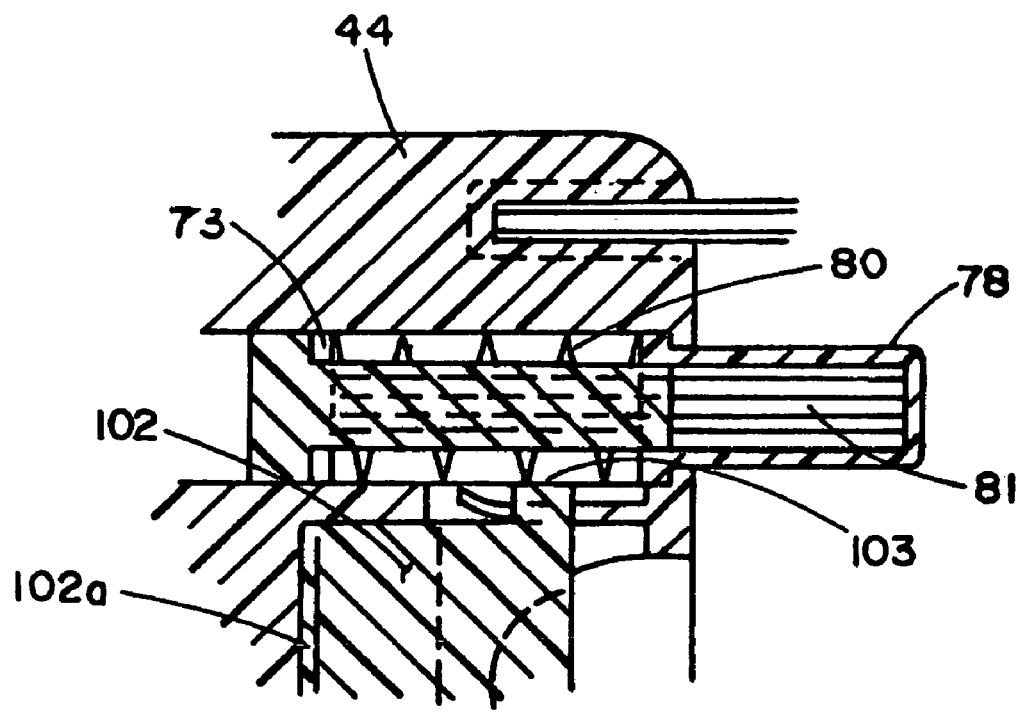
FIG. 6 is a cross-sectional view similar to FIG. 5, but showing the rate control knob of the device in a retracted, starting position.

To release the selector means from the locked position shown in FIG. 5 so that it can return to the starting position shown in FIG. 6, novel release means are provided. This release means here comprises a release member 102 and lock tab release 103 which are slidably mounted within cover 44 for movement against the urging of a spring 102*a* which is connected to release member 102. It is to be observed that release member 102 is movable against the urging of spring 102*a* from the first position shown in FIG. 5 to a second, inward position shown in FIG. 6. As best seen in FIG. 5, release member 102 is provided with a channel 104 that slidably receives yieldably deformable leaf spring 88. With this construction, as the release member is moved toward the inward position shown in FIG. 6, spring 88 will travel within channel 104 in a manner to cause it to move downwardly into the flattened configuration shown in FIG. 6. As the spring is thusly wiped downwardly by the walls of channel 104, end 88*a* of the spring will move out of the indexing cavity within which it resides so as to permit spring 88 to return to its starting position and in so doing will permit spring 80 to move indexing knob 78 to the outward position shown in FIG. 6. In this outward position, the release means has released the leaf spring from the indexing cavity so that the indexing knob can be once again rotated to a second position to align the selector means with another outlet port of rate control cover 45 and with another of the micro channels formed in rate control plate 46 so as to permit fluid flow from the source of fluid toward the fluid delivery line 38 at a second flow rate. As indicated in FIG. 1, portion 44*a* of cover 44 is provided with a viewing window 44*b* which permits the caregiver to view indicating indicia 105 (FIG. 1) that are provided on selector portion 76*a* which show the flow rate selected. Indicia 105 comprise a portion of the indicator means of the invention for indicating the rate of fluid flow from the fluid source toward the fluid delivery.

To enable the device to be interconnected to a patient or to another object, an adhesive backed foam member 106 is connected to base 42 (see FIG. 13).

Figure 27:
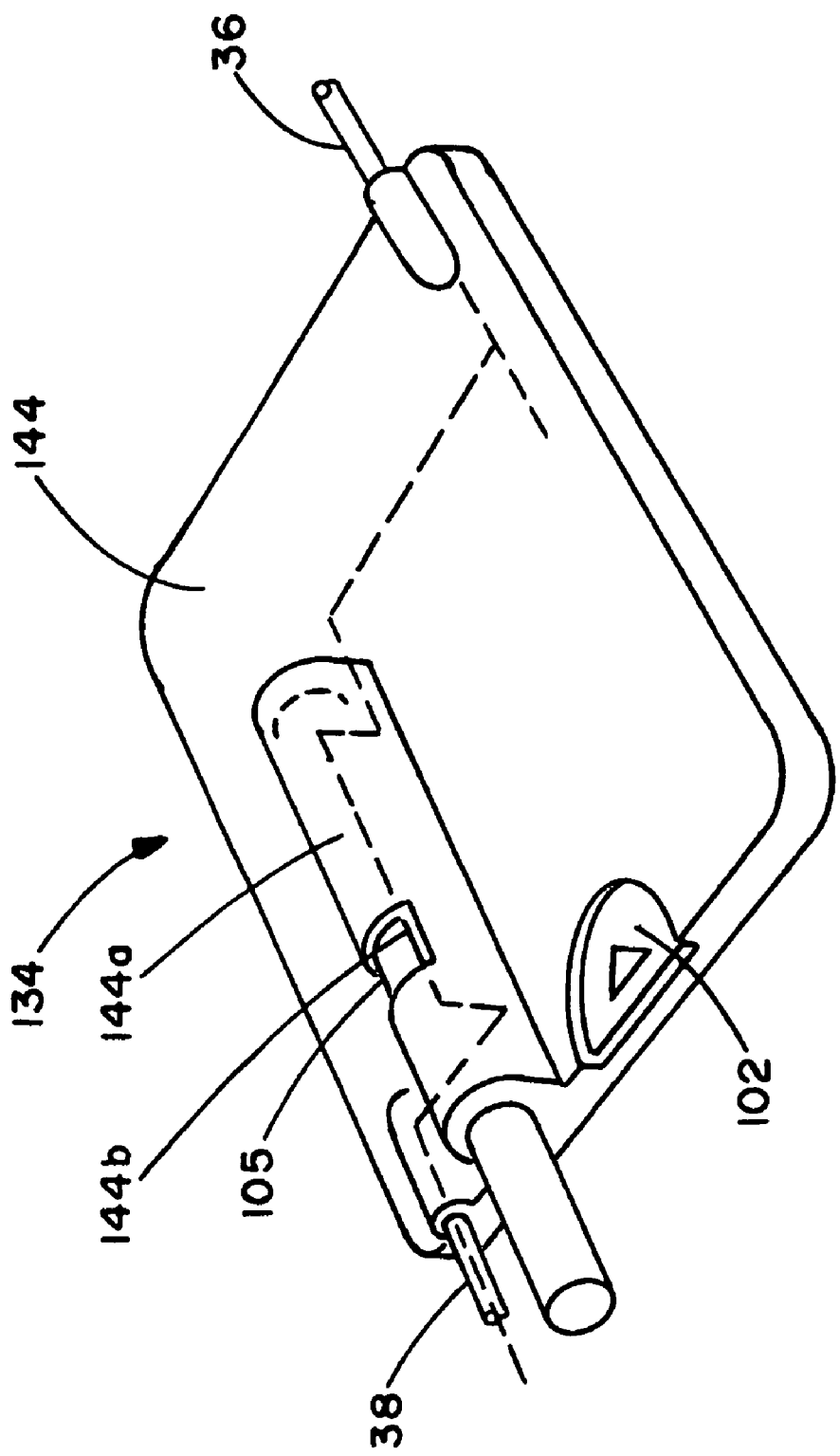
FIG. 27 is a generally perspective view of an alternate form of the in-line flow rate control device of the invention.

Turning next to FIGS. 27 through 41, an alternate form of the fluid flow rate control device of the present invention is there illustrated and generally designated by the numeral 134. This device is similar in many respects to the device shown in FIGS. 13 through 26 and like numerals are used in FIGS. 27 through 41 to identify like components. As illustrated in FIG. 27, the device is adapted to be interposed between a fluid supply line 36 which is interconnected with a source of fluid under pressure and a fluid delivery line 38 which can be interconnected with a remote site to which the fluid is to be delivered at a controlled rate.

Figure 28:
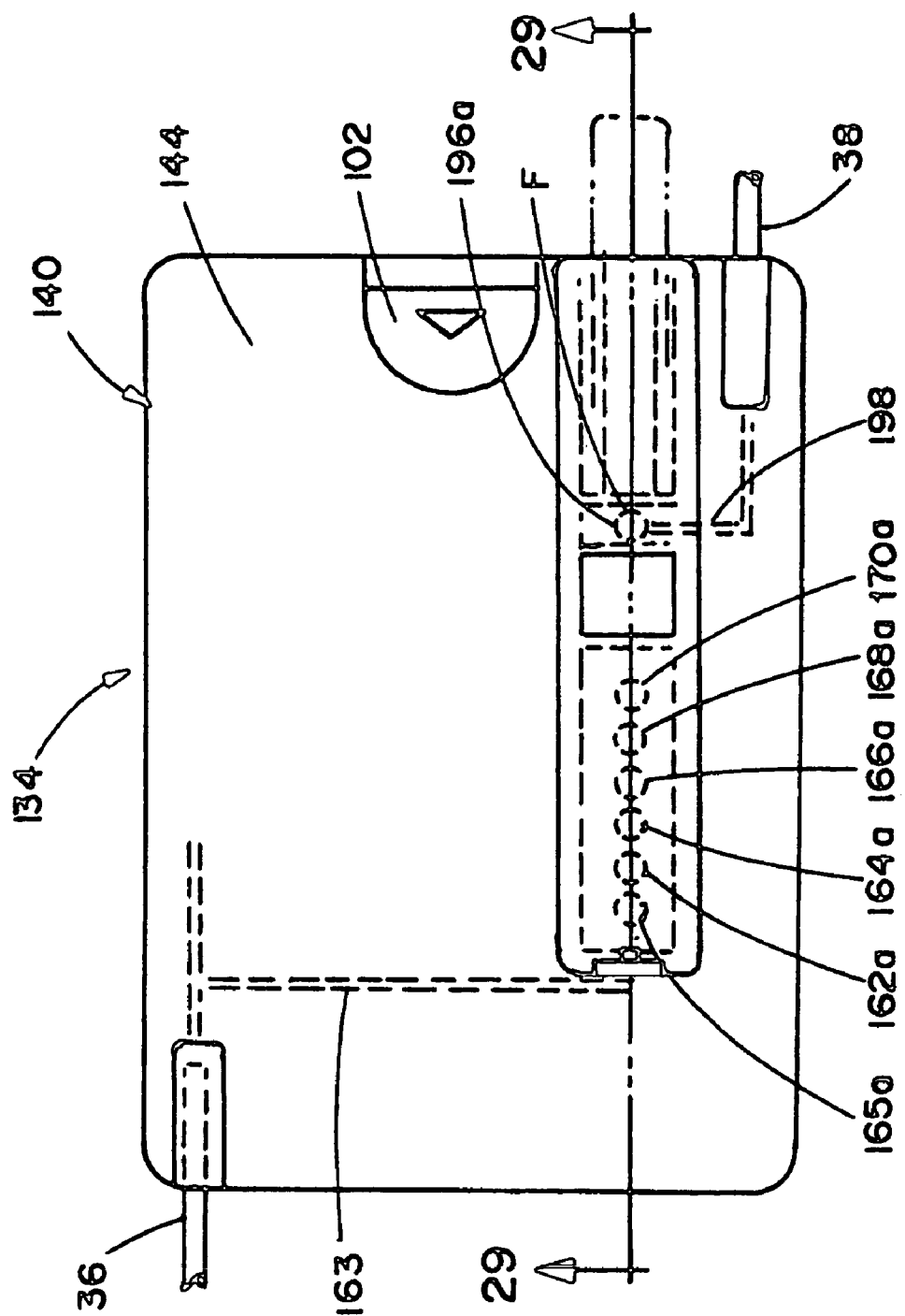
FIG. 28 is a top plan view of the device shown in FIG. 27.
Figure 29:
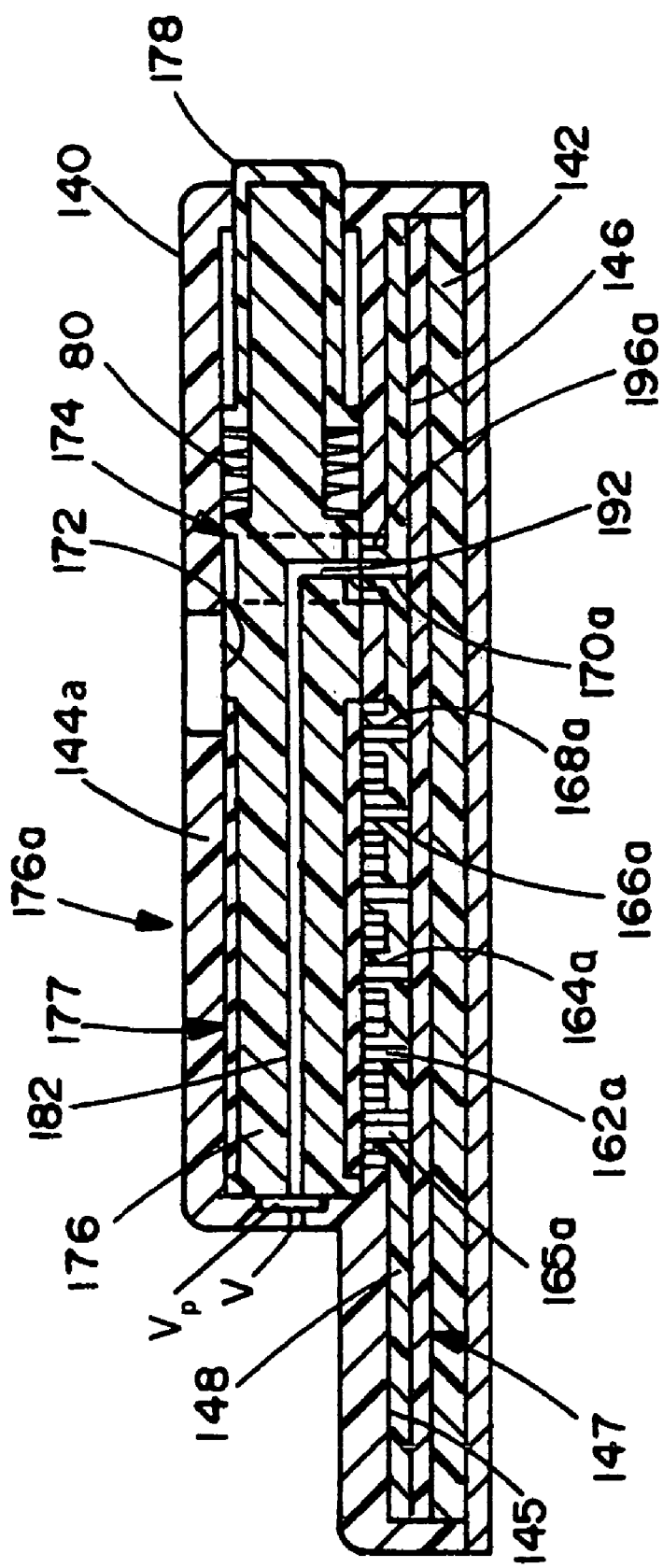
FIG. 29 is a cross-sectional view taken along lines 29-29 of FIG. 28.

As illustrated in FIGS. 28 and 29, the device of the latest form of the invention comprises a hollow housing 140 which is made up of a base portion 142 and an interconnected cover portion 144. Base portion 142 cooperates with cover 144 to define an internal chamber 145 (FIG. 29). Disposed within chamber 145 is one portion of the important flow control means of the invention for controlling fluid flow from the fluid supply line 36 toward the fluid delivery line 38. In this latest embodiment of the invention, the flow control means is similar to the flow control means earlier described herein and comprises a flow rate control assembly, generally designated as 147, which is housed within chamber 145 and a cooperating selector means for selecting the desired rate of fluid flow from the fluid source toward the fluid delivery line. The primary difference between this latest flow rate control means of the invention and that previously described concerns the provision of priming means for initially priming the fluid flow lines prior to the actual delivery of the medicinal fluids to the patient.

Figure 30:
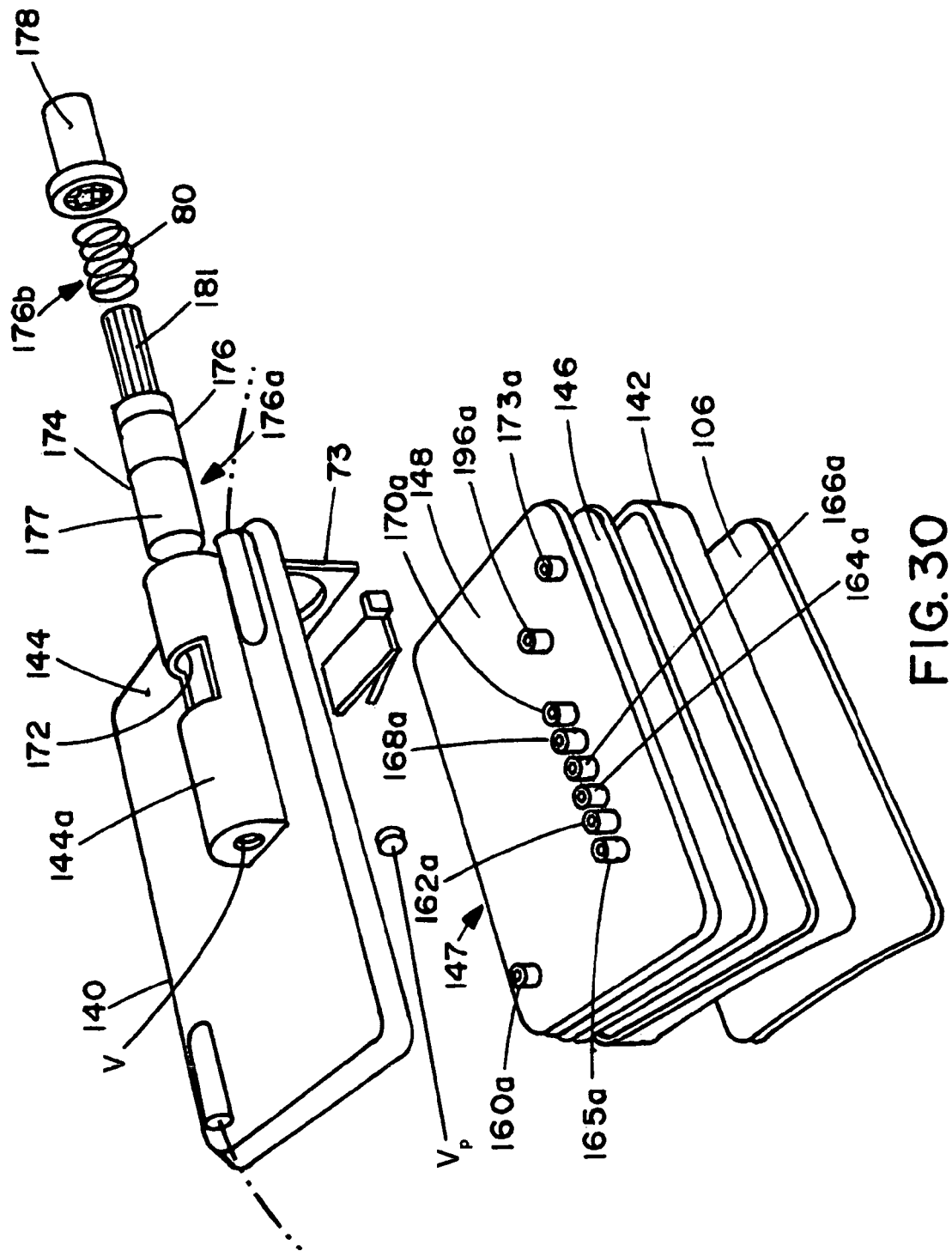
FIG. 30 is a generally perspective, exploded view of the device shown in FIGS. 27 through 29.
Figure 31:
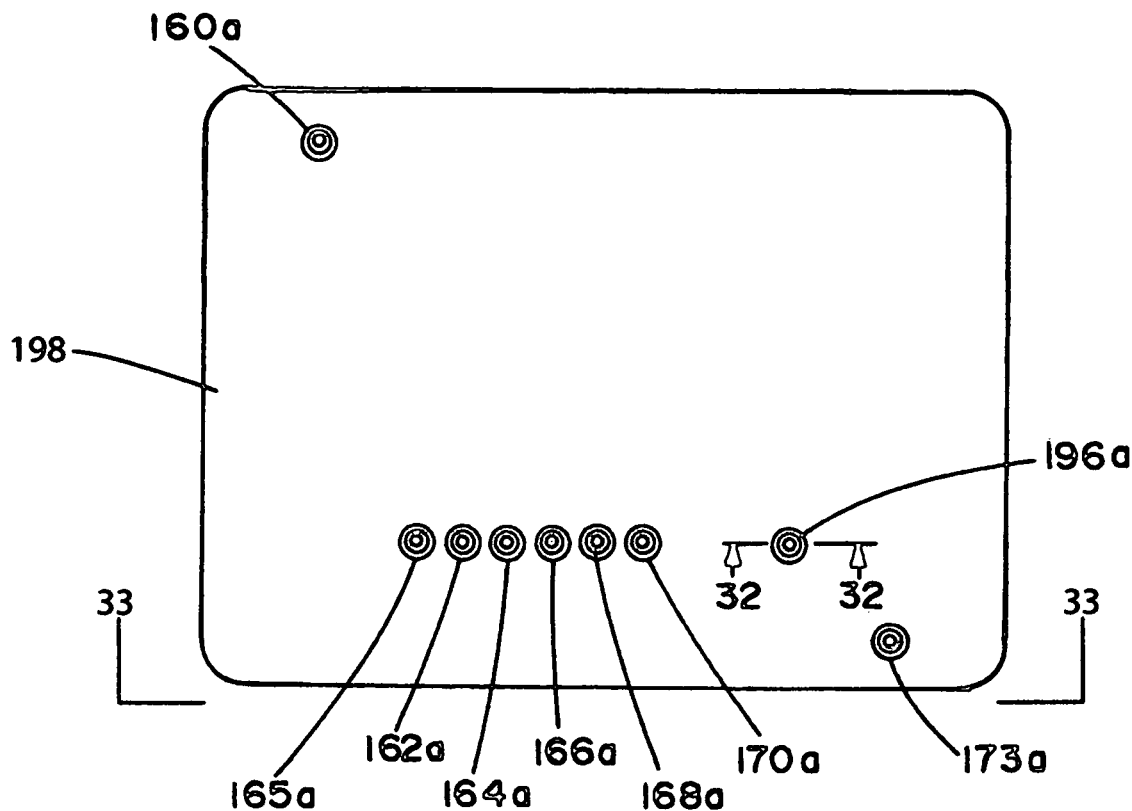
FIG. 31 is a top plan view of the cover member of the flow rate control assembly of the apparatus illustrated in FIG. 27.
Figure 33:
FIG. 33 is a view taken along lines 33-33 of FIG. 31.
Figure 32:
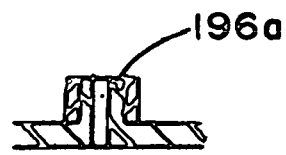
FIG. 32 is an enlarged cross-sectional view taken along lines 32-32 of FIG. 31.
Figure 34:
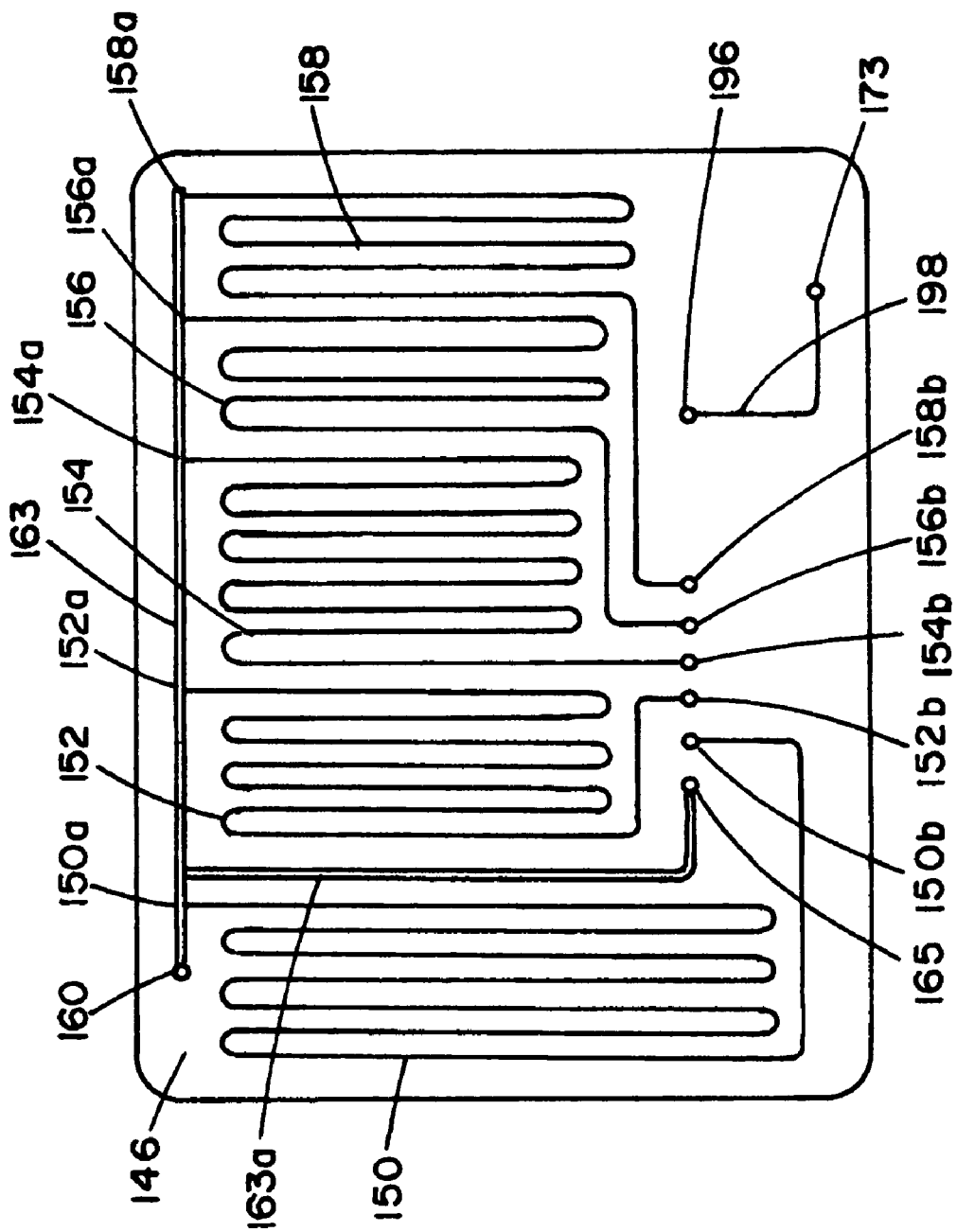
FIG. 34 is a top plan view of the rate control member of this latest form of the invention.
Figure 41:
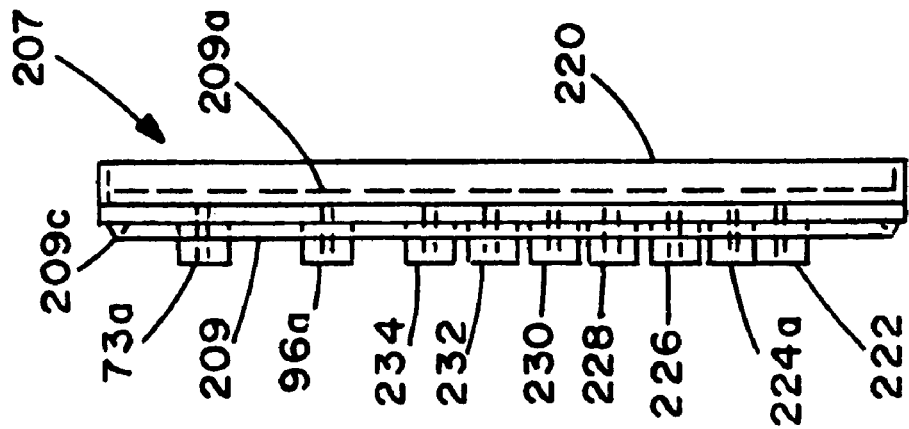
FIG. 41 is a side view of an alternate form of flow rate control assembly of the present invention.
Figure 42:
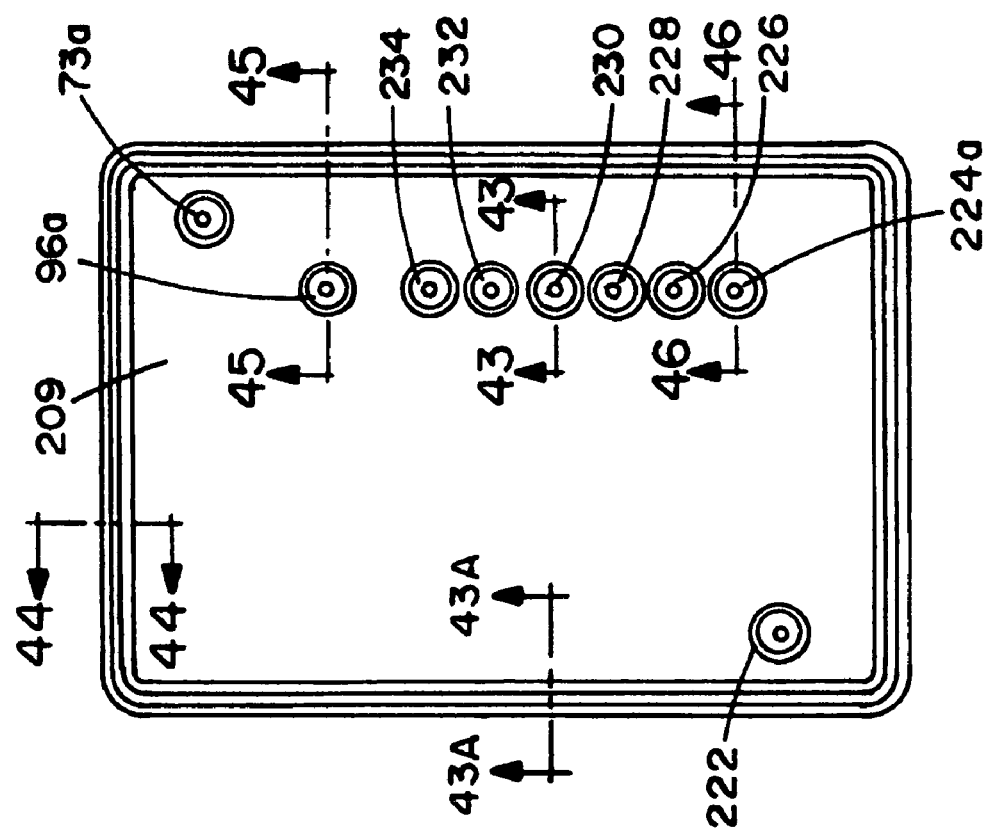
FIG. 42 is a top plan view of the flow rate control assembly of the apparatus illustrated in FIG. 41.

Considering first the flow rate control assembly 147, this important component of the flow control means comprises a rate control plate 146 and an interconnected rate control cover 148 (FIG. 30). As best seen in FIG. 34, rate control plate 146 is provided with a plurality of fluidic micro channels identified as 150, 152, 154, 156 and 158. Each of the fluidic micro channels is in communication with the rate control plate inlet 160 via the novel priming means of the invention for purging and priming the various fluid delivery passageways of the flow control means. An advantage of this latest form of the device over that previously described is the provision of this important novel priming means, which comprises prime channel 163 and which functions to purge gases from delivery line 38 and to prime the various fluidic elements of the device before the fluid is delivered to the fluid delivery line 38. This feature of the device ensures that only the desired fluid is delivered at the outlet port of the device during normal operation and that the device is in a state in which it will deliver fluid at the exit of the output capillary in as short a time as possible. In this regard it is to be noted that the fluidic micro channels are provided with inlets 150*a*, 152*a*, 154*a*, 156*a* and 158*a* respectfully (FIG. 34). These inlets are in communication with prime channel 163 so that as the prime channel is filled, via filter means, each of the fluidic micro channels will also fill. Prime channel 163 is also in communication with a prime channel outlet port 165, which, in turn, communicates with cover outlet port 165*a* (FIG. 30) formed in cover 148. Cover outlet port 165*a* aligns with an inlet to the flow rate control assembly, the details of construction of which will presently be described. As the various fluid flow passageways of the device fill with fluid during the priming step, gases contained within the passageways will be vented to atmosphere via a vent "V" formed in cover 144 (FIG. 29). The vent "V" preferably comprises a porous hydrophobic material such as a plastic. The pores of the vent should have a diameter of no more that 2 μm. It is well known that aqueous fluid will not move through capillaries (holes) on the order of 2 μm in diameter in hydrophobic material under the pressures contemplated for use in this device of this latest form of the invention (pressures of approximately 1 ATM or less). However, there are also commercial hydrophobic porous vents made from sintered porous polyethylene available from companies such as the Porvair Filtration Group. Many of these vents have pore sizes of 10-100 microns and are commonly used as medical fluid vent plugs. Vent "V" could also be provided in the form of a cylinder with a diameter of approximately 1 mm and a length of approximately 1 mm.

The fluidic micro channels are also provided with outlets 150*b*, 152*b*, 154*b*, 156*b* and 158*b* respectfully (FIG. 34). These outlets align with cover outlet ports 162*a*, 164*a*, 166*a*, 168*a*, and 170*a* respectively when the flow rate control assembly is assembled together in the manner illustrated in FIG. 29. When the flow rate control assembly is assembled together, cover inlet port 160*a* (FIG. 30) aligns with rate control plate inlet 160 (see FIG. 34).

As previously discussed in connection with a first embodiment of the invention, each of the outlet ports formed in rate control cover 148 can be placed in selective communication with the fluid delivery line 38 by manipulation of the rate control means of the invention. In this way, the rate of fluid flow toward the fluid delivery line can be can be precisely controlled by the caregiver.

As earlier described herein, the fluidic micro channels formed in rate control plate 146 of this latest form of the invention may be of different sizes, lengths and configurations as shown in FIG. 34. Further, the flow control fluidic micro channels may be rectangular in cross-section, or alternatively, can be semicircular in cross-section, U-shaped in cross-section, or they may have any other cross-sectional configuration that may be appropriate to achieve the fluid flow characteristics that are desired in the particular end-use application.

As best seen in FIGS. 27, 29 and 30, cover 144 is provided with an, upraised portion 144a that defines an elongated, generally cylindrically-shaped chamber 172 (FIG. 29). Sealably receivable within chamber 172 and supported by a retainer member 73, is the second component of the flow control means of the invention, namely the selector means, or rate control selector assembly 174. This important rate control selector assembly is similar in construction and operation to the previously described control selector assembly 74 and includes a rate control shaft assembly 176, a cooperating control knob 178 and an operating spring 80. As illustrated in FIGS. 29 and 30 of the drawings, rate control shaft assembly 176 includes a selector portion 176a and a control portion 176b. As indicated in FIG. 30, selector portion 176a includes a generally cylindrically-shaped rate control shaft 177 that is provided with a longitudinally-extending fluid flow passageway 182 and a plurality of radially-extending passageways 184, 186, 188, 190 and 192 that communicate with passageway 182 (FIG. 35). Passageway 182 also communicates with the radially-extending passageway 193, which communicates with a priming channel 163 via a rate control cover port 165a. With this construction, as the priming channel is filled, all of the fluid flow passageways formed in rate control shaft 177 will be primed or filled with the medicinal fluid dispensed to the fluid delivery line 36.

As in the earlier described embodiment of the invention, rotation of the rate control shaft assembly 176 within chamber 172 will permit a selected one of the radially-extending passageways formed in shaft 177 to be aligned with a selected one of the outlet ports of cover 148 and also with a selected one of the fluidic micro channels formed in rate control plate 146. To ensure proper mating of the selector portion 176a and the control portion 176b, the selector portion includes a groove 179 and the control portion includes a spline 179a, which is received within groove 179 (see FIGS. 35 and 37).

As illustrated in FIGS. 30, 35 and 38, the shank portion 181 of the rate control portion 176b of the rate control assembly is knurled and control knob 178 is grooved (FIG. 30) so that when the control knob is mated with the rate control portion 176a in the manner shown in FIG. 29, rotation of the control knob will impart rotation to the selector portion 176a of the rate control shaft assembly. As previously mentioned, controlled rotation of selector portion 176a will cause one of the radially-extending passageways formed within shaft 177 to be moved into fluid communication with a selected one of the outlets of the fluidic rate control channels formed in the rate control plate 146.

Before further discussing the operation of the selector means of the invention, it should be understood that the various methods of making the rate control plate of this latest form of the invention and materials that can be used to construct the rate control plate are substantially the same as the methods discussed in connection with rate control plate 46.

Another important feature of the invention comprises locking means for locking the selector means in position after a particular fluid flow micro channel has been selected by means of the controlled rotation of the selector knob 178. This locking means is substantially identical in construction and operation to the locking means discussed in connection with the earlier described embodiment of the invention and reference should be made to this earlier discussion for a description of the construction and operation of the locking means of this latest form of the invention.

In operation of the device of this latest form of the invention, with the locking means in the locked position, the rate control assembly is first rotated so that radial passageway 193 is aligned with cover outlet port 165a. This permits fluid to flow from plate inlet 160 into prime channel 163, into each of the fluidic micro channels and into radial passageway 193 via prime channel leg 163a, plate outlet 165 and cover outlet port 193. From radial passageway 193, the fluid will flow into longitudinal passageway 182 and then toward delivery line 38.

Following priming of the fluid flow passageways, the rate control assembly can be rotated in a manner to place a selected radial passageway, such as, for example, passageway 184, into alignment with cover outlet port 162a. In this orientation fluid will flow from the fluid source, through fluidic micro channel 150 at a precise rate and into cover outlet port 162a via plate outlet 156b. From outlet port 162a, the fluid will flow into radial passageway 184 and then into the previously primed axial passageway 182. From axial passageway 182 fluid will flow through a filter 90 (FIG. 37), which is carried by the control knob shaft assembly 176, into an axially-extending fluid passageway 192 formed in control portion 176b and then into an annular passageway 194 formed in the enlarged diameter portion 176d of control portion 176b. By controllably rotating the rate control assembly, any one of the fluidic micro channels can be similarly placed in fluid communication with a fluid delivery line 38 in the manner next to be described.

When the selector means is selectively aligned with one of the outlets of the fluidic micro channels, the fluid can flow freely into the selector portion of the selector means via the selected radially-extending fluid passageways formed in the selector portion 176a. Filter 90, which filters the fluid flowing through the fluid flow path toward the fluid delivery line, can be constructed from any suitable material including sintered metal, porous glass, porous ceramic, porous plastic, or like material of a character well known to those skilled in the art.

From annular passageway 194, the fluid will flow at a controlled rate through the fluid flow path into an inlet port 196a formed in cover 148 which incorporates a filter "F" and then into an inlet 196, which is formed in rate control plate 146 and is aligned with inlet port 196a (see FIG. 29). Filter "F" may comprise a porous polymer, porous ceramic or like material that may be hydrophilic or hydrophobic in nature depending on the fluid being transported. From inlet 196, the fluid will flow to outlet 173 via a passageway 198 formed in rate control plate 146, into outlet port 173a and then from the fluid flow path into the fluid delivery line 38 which is in communication with outlet port 173a (see FIGS. 33 and 34).

It is important to note that priming of the various fluid passageways of the device ensures that only the desired fluid is delivered at the output of the device during normal operation and that the device is in a state in which it will deliver fluid at the exit of the administration line in a reasonably short time. The value of the priming means of this latest form of the invention is evident from a study of FIG. 55 of the drawings which comprises a table of the fluidic properties of one form of the flow rate control member, or chip 46, the flow rate selector means and the administration line for the distal rate control device of this latest form of the invention. For purposes of illustration in FIG. 55, the flow rates are shown to be from 0.1 to 5.00 ml/hr and the rate defining channels are assumed to be 4000 $\mu m^2$ to 40,000 $\mu m^2$. Similarly, the priming channel is assumed to be 100,000 $\mu m^2$, the channel in the rate control selector means is assumed to be 1 mm in diameter and 3 cm long and the administration line is assumed to be 1 meter long and 40 thousandths of an inch internal diameter.

The priming channels on the chip, the channel in the flow rate selector means and the administration line are treated as one item for the purpose of priming time and flow rate.

From a study of FIG. 55 it can be seen that if one of the flow rate defining fluidic micro channels were used to prime the administration line, then there would be an unreasonably long time between the time that the device is initially "turned on" and the time that fluid is delivered from the administration line. This is because the volume of the administration line is 0.785 ml. For example, suppose the flow rate is 0.5 ml/hr then it would be 94 minutes (i.e., 0.785 ml/0.5 ml/hr=1.57 hours) before fluid emerges from the administration line and the device is ready to use. This length of time to wait before the device is ready to use is undesirable in most applications of the device. It is evident that a priming means envisioned by this latest form of the device of the invention is an advantageous feature which enables the device be ready to administer fluid in a matter of a minute or less.

If the fluidic system is not compatible with the fluid being transported, either in terms of its biocompatibility or hyrdophilicity characteristics, a surface modification process will be needed. While not wanting to be held to a particular approach, the surface modification methodology may take one of several forms. One process that is extremely clean, fast and effective is plasma processing. In particular this technique allows for any of the following 1) plasma activation, 2) plasma induced grafting and 3) plasma polymerization of molecular entities on the surface of the bellows. For cases where an inert hydrophobic interface is desired, plasmas using hydrophilic molecules may be employed. That is, the channels' surface may be cleaned with an inert gas plasma, and subsequently, an appropriate plasma may be used to graft these molecule to the surface. Alternatively, if a hydrophobic surface is desired (e.g. for solutions that are highly corrosive or in oil-based solvents) an initial plasma cleaning may be done, followed by a plasma polymerization using hydrophobic monomers.

To release the selector means from the locked position so that it can return to the starting position, novel release means are provided. This release means is identical in construction and operation to the release means discussed in connection with the previously described embodiment and reference should be made to the earlier discussion for an understanding of the construction and operation of this important release means.

As indicated in FIG. 27, portion 144a of cover 144 is provided with a viewing window 144b, which permits the caregiver to view indicating indicia 105 that are provided on selector portion 176a, which show the flow rate selected. Indicia 105 comprise a portion of the indicator means of the invention for indicating the rate of fluid flow from the fluid source toward the fluid delivery.

To enable the device to be interconnected to a patient or to another object, an adhesive backed foam member 106 is connected to base 142 (see FIG. 30).

Turning next to FIGS. 42 through 54, an alternate form of flow rate control assembly is there illustrated and generally designated by the numeral 207. Flow rate control assembly 207 is usable with the apparatus shown in FIG. 29 of the drawings and is adapted to be disposed within chamber 145 of the device housing. This alternate form of the flow rate control assembly is also adapted to cooperate with the selector means of the apparatus of FIG. 29 in a manner previously described to select the desired rate of fluid flow from the fluid source toward the fluid delivery line.

The primary difference between this latest flow rate control assembly and that previously described is that the fluidic micro flow channels which control the rate of fluid flow are formed in the lower surface 209a of the rate control cover, 209 of the assembly (see FIG. 49). More particularly, lower surface 209a of cover 209 is provided with a plurality of micro channels identified as 210, 212, 214, 216 and 218. When the rate control base 220 of a rate control assembly is sealably interconnected with cover 209 in the manner shown in FIG. 41, the plurality of micro channels will be sealed to form a plurality of fluid carrying fluidic micro channels. In this regard, it is to be noted that a circumferentially extending recess 209b is formed in cover 209. It is also to be observed that cover 209 is provided with a circumferentially extending, sonic energy director 209c, which enables the cover member to be sonically bonded to the apparatus housing 180 when the alternate form of rate control assembly is positioned within chamber 145. Sealably receivable within recess 209b is an upstanding, circumferentially extending step 220a formed on base 220.

Each of the fluidic micro channels is in communication with the rate control inlet 222 via the priming means of the invention for purging and priming the various fluid delivery passageways of the flow control means. This priming means here comprises a prime channel 223 which functions to purge gases from delivery line 38 and to prime the various fluidic elements of the device before the fluid is delivered to the fluid delivery line 38. It is to be noted that the fluidic micro channels are provided with inlets 210a, 212a, 214a, 216a and 218a respectfully (FIG. 49). These inlets are in communication with prime channel 223 so that as the prime channel is filled, each of the fluidic micro channels will also fill. Prime channel 223 is also in communication with a prime channel outlet port 224, which, in turn, communicates with cover outlet port 224a (FIGS. 47 and 48) formed in cover 209. Cover outlet port 224a aligns with an inlet to the flow rate control assembly, the details of construction of which were described in connection with a description of the previously embodiment of the invention. As the various fluid flow passageways of the device fill with fluid during the priming step, gases contained within the passageways will be vented to atmosphere via a vent "V" formed in cover 144 (FIG. 29).

The fluidic micro channels are also provided with outlets 210b, 212b, 214b, 216b and 218b respectfully (FIG. 49). These outlets align with cover outlet ports in FIGS. 43 and 43a, the upstanding 226, 228, 230, 232, and cover 234 respectively (FIG. 47). As indicated, outlet ports are formed from an elastomeric material "EM" that compresses when the cover and base are mated as shown in FIG. 43A. This compression of the parts which comprise the port sealing means, prevents fluid leakage about the ports.

As previously discussed in connection with the earlier described embodiment of the invention, each of the outlet ports formed in rate control cover 209 can be placed in selective communication with the fluid delivery line 138 via port 96a, channel 98 and port 73a by manipulation of the rate control means of the invention. In this way, the rate of fluid flow toward the fluid delivery line can be can be precisely controlled by the caregiver. Gasses trapped within the fluid flow channels can be vented to atmosphere via vents VR and VC.

As earlier described herein, the fluidic micro channels formed in cover 209 of this latest form of the invention may be of different sizes, lengths and configurations as shown in FIG. 49. Further, the flow control fluidic micro channels may be rectangular in cross-section, or alternatively, can be semicircular in cross-section, U-shaped in cross-section, or they may have any other varying cross-sectional configuration that may be appropriate to achieve the fluid flow characteristics that are desired in the particular end use application.

The delivery of fluid without delivering air at the same time (even though the relative amount of air is very small compared to the amount of fluid delivered) is highly desirable. Therefore, part of the distal rate control invention includes the use of vent means to remove air from the fluidic system itself. Vent means for the fluidic system could be placed in several locations including: in the rate control chip, distal to the rate control chip, or in the selector means.

The purpose of the vent means is to allow for any air that is present in the device before liquid is presented to the device or that evolves out of the fluid in the device over time during normal operation to exit from the fluid path before fluid reaches the end of the delivery line.

For some applications it might be sufficient to have vent means in the form of a vent in the delivery line 38 at some point downstream from the chip. This type of vent and filter is common for use in the delivery of medical fluids. An example is a hydrophobic-hydrophilic IV vent-filter made from polytetrafluoroethene (PTFE) available from Qosina Corporation. For some applications an on-chip vent is also desirable for convenience, safety or compactness.

The vents of the vent means are preferably composed of a porous hydrophobic material such as a plastic. The pores should have a diameter of no more than 2 µm. It is well known that aqueous fluid will not move through capillaries (hopes) on the order of 2 µm in diameter in hydrophobic material under the pressures contemplated for use in this device (pressures of approximately 1 ATM or less). However, there are also commercial hydrophobic porous vents made from sintered porous polyethylene available from companies such as the Porvair Filtration Group. Many of these vents have pore sizes of 10-100 microns and are commonly used as medical fluid vent plugs. The vents could be in the form of a cylinder with a diameter of approximately 1 mm and a length of approximately 1 mm.

The above vents VR when located on the fluidic chip would reside on control plates 46 and 209 (FIGS. 17 and 49) in such a way that the material composing the vent provides a passageway for air from the channel 98 below through the vent to the external environment via a cylindrical hole VC of the same diameter extending through the rate control plate cover 48 and 209 (FIGS. 13 and 48).

As shown in FIGS. 43A and 49A, the surfaces of the various fluidic microchannels have been modified to provide unique surface characteristics. More particularly, the surfaces have been coated with a biocompatible coating "C".

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A flow rate control device for controlling the rate of fluid flow between a fluid supply line which is connected to a source of fluid and a fluid delivery line which delivers the fluid to a remote location, said flow rate control device comprising:
   (a) a housing having a cover, a base and an internal chamber, said internal chamber having an inlet in communication with said fluid supply line, an outlet in communication with said fluid delivery line and a flow path between said inlet and said outlet; and
   (b) flow rate control means carried by said housing for controlling the rate of fluid flow toward said delivery line, said flow rate control means comprising:
       (i) a rate control assembly disposed within said internal chamber of said housing, said rate control assembly including a base and a cover connected to said base, one of said cover and said base having a plurality of fluidic micro channels formed therein, each said fluidic micro channel having a length, width and cross-sectional area and an inlet in communication with said supply line and an outlet in communication with said fluid delivery line; and
       (ii) a rate control selector assembly operably interconnected with said rate control assembly, said rate selector assembly including a rate control shaft assembly comprising a generally cylindrically-shaped rate control shaft carried by said housing for rotation with respect thereto, said shaft having a plurality of radially extending fluid flow passageways formed therein.

2. The device as defined in claim 1 further including indicator means associated with said rate control means for indicating the rate of fluid flow toward the remote location.

3. The device as defined in claim 1 in which said rate control shaft has a longitudinally-extending fluid flow passageway, said plurality of radially-extending fluid flow passageways being in communication with said longitudinally-extending fluid flow passageway.

4. The device as defined in claim 1 in which said rate control selector assembly further includes a control knob operably associated with said rate control shaft, for imparting rotation thereto, said rate control knob being movable between a first extended position and a second position.

5. The device as defined in claim 4 further including locking means carried by said housing for releasably locking said control knob against rotation.

6. The device as defined in claim 5 in which said control knob is provided with a plurality of circumferentially spaced-apart indexing cavities and in which said locking means comprises a locking spring having a distal end lockably receivable within a selected one of said indexing cavities.

7. The device as defined in claim 6 further including release means for releasing said distal end of said locking spring from said selected one of said indexing cavities.

8. The device as defined in claim 7, in which said release means comprises a release member slidably mounted within said cover for movement between first and second positions.

9. The device as defined in claim 8 in which said release means further comprises a spring for yieldably resisting movement of said release member toward said second position.

10. A flow rate control device for controlling the rate of fluid flow between a fluid supply line which is connected to a source of fluid and a fluid delivery line which delivers the fluid to a remote location, said flow rate control device comprising:
   (a) a housing having a housing cover, a housing base and an internal chamber, said internal chamber having an inlet in communication with said fluid supply line, an outlet in communication with said fluid delivery line and a flow path between said inlet and said outlet; and
   (b) flow rate control means carried by said housing for controlling the rate of fluid flow toward said delivery line, said flow rate control means comprising:
       (i) a rate control assembly disposed within said internal chamber of said housing, said rate control assembly including a rate control base and a rate control cover connected to said rate control base, a selected one of said rate control base and said rate control cover having a plurality of fluidic micro channels formed therein, each said fluidic micro channel being of a selected length and width and having an inlet in communication with said supply line and an outlet in communication with said fluid delivery line; and (ii) a rate control selector assembly operably interconnected with said rate control assembly, said rate selector assembly including a rate control shaft assembly carried by said housing for rotation with respect thereto, said rate control shaft assembly comprising a shaft having a longitudinally-extending fluid flow passageway and a plurality of radially-extending fluid flow passageways in communication with said longitudinally-extending fluid flow passageway, said rate control shaft being rotatable relative to said housing to cause a selected one of said radially extending fluid flow passageways to communicate with a selected one of said fluidic micro-channels.

11. The device as defined in claim 10 in which said flow rate control means further comprises priming means for priming said plurality of fluidic micro channels, said longitudinally-extending fluid flow passageway and said plurality of radially-extending fluid flow passageways of said rate control shaft assembly with fluid from said fluid supply line.

12. The device as defined in claim 10 in which said rate control assembly further includes vent means for venting to atmosphere air contained within said fluidic micro channels.

13. The device as defined in claim 10 in which said selector assembly further includes a control knob operably associated with said rate control shaft, for imparting rotation thereto, said rate control knob being movable between a first extended position and a second position.

14. The device as defined in claim 13 further including locking means carried by said housing for releasably locking said control knob against rotation.

15. The device as defined in claim 14 in which said control knob is provided with a plurality of circumferentially spaced-apart indexing cavities and in which said locking means comprises a locking spring having a distal end lockably receivable within a selected one of said indexing cavities.

16. The device as defined in claim 15 further including release means for releasing said distal end of said locking spring from said selected one of said indexing cavities.

17. A flow rate control device for controlling the rate of fluid flow between a fluid supply line which is connected to a source of fluid and a fluid delivery line which delivers the fluid to a remote location, said flow rate control device comprising:

(a) a housing having a housing cover, a housing base and an internal chamber, said internal chamber having an inlet in communication with said fluid supply line, an outlet in communication with said fluid delivery line and a flow path between said inlet and said outlet; and (b) flow rate control means carried by said housing for controlling the rate of fluid flow toward said delivery line, said flow rate control means comprising:

(i) a rate control assembly disposed within said internal chamber of said housing, said rate control assembly including a rate control base and a rate control cover, a selected one of said rate control base and said rate control cover having a plurality of fluidic micro channels formed therein, each said fluidic micro channel having an inlet in communication with said supply line and an outlet in communication with said fluid delivery line; and (ii) a rate control selector assembly operably interconnected with said rate control assembly, said rate selector assembly including:

a. a rate control shaft assembly carried by said housing for rotation with respect thereto, said rate control shaft assembly comprising a shaft having a longitudinally-extending fluid flow passageway and a plurality of radially-extending fluid flow passageways in communication with said longitudinally-extending fluid flow passageway;

b. a control knob operably associated with said rate control shaft, for imparting rotation thereto to cause a selected one of said plurality of radially extending fluid flow passageways to communicate with a selected one of said plurality of fluidic micro-channels, said rate control knob being movable between a first extended position and a second position; and c. locking means carried by said housing for releasably locking said control knob against rotation; and (iii) priming means for priming said plurality of fluidic micro channels, said longitudinally-extending fluid flow passageway and said plurality of radially-extending fluid flow passageways of said rate control shaft assembly with fluid from said fluid supply line.

18. The device as defined in claim 17, further comprising vent means carried by said housing and in communication with said longitudinally-extending fluid flow passageway for venting to atmosphere gases contained within plurality of fluidic micro channels, said longitudinally-extending fluid flow passageway and said plurality of radially-extending fluid flow passageways of said rate control shaft assembly.

19. The device as defined in claim 17 in which said fluidic microchannels have surfaces, said surfaces being modified to provide unique surface characteristics.

20. The device as defined in claim 17 in which said rate control assembly further includes sealing means for substantially sealing said shaft relative to said housing.

21. The device as defined in claim 17 in which said rate control cover includes upstanding outlet ports each said outlet port including port sealing means for preventing fluid leakage about said outlet ports.

22. The device as defined in claim 17 further including a filter for filtering the fluid flowing from said supply line toward said fluidic microchannels.

23. The device as defined in claim 18 in which said control knob is provided with a plurality of circumferentially spaced-apart indexing cavities and in which said locking means comprises a locking spring having a distal end lockably receivable within a selected one of said indexing cavities.

24. The device as defined in claim 18 further including release means for releasing said distal end of said locking spring from said selected one of said indexing cavities.

25. The device as defined in claim 24, in which said release means comprises a release member slidably mounted within said cover for movement between first and second positions.

26. The device as defined in claim 25 in which said release means further comprises a spring for yieldably resisting movement of said release member toward said second position.

27. The device as defined in claim 26 further including indicator means associated with said rate control means for indicating the rate of fluid flow toward the remote location.

* * * * *